(12) United States Patent
Salceda et al.

(10) Patent No.: US 7,238,471 B1
(45) Date of Patent: Jul. 3, 2007

(54) METHOD OF DIAGNOSING, MONITORING, STAGING, IMAGING AND TREATING BREAST CANCER

(75) Inventors: Susana Salceda, San Jose, CA (US); Robert Cafferkey, San Jose, CA (US); Herve Recipon, San Francisco, CA (US); Yongming Sun, San Jose, CA (US)

(73) Assignee: DiaDexus, Inc., South San Francisco, CA (US)

( * ) Notice: Subject to any disclaimer, the term of this patent is extended or adjusted under 35 U.S.C. 154(b) by 348 days.

(21) Appl. No.: 09/721,183

(22) Filed: Nov. 22, 2000

Related U.S. Application Data

(60) Provisional application No. 60/166,973, filed on Nov. 23, 1999.

(51) Int. Cl.
*C12Q 1/68* (2006.01)
*G01N 33/48* (2006.01)

(52) U.S. Cl. .............................................. 435/6; 436/64
(58) Field of Classification Search ...................... 435/4
See application file for complete search history.

(56) References Cited

U.S. PATENT DOCUMENTS

| | | | |
|---|---|---|---|
| 4,690,914 A | 9/1987 | Callut et al. | 502/400 |
| 5,585,103 A | 12/1996 | Raychaudhuri et al. | 424/278.1 |
| 5,985,270 A | 11/1999 | Srivastava | 424/93.71 |
| 6,432,707 B1 * | 8/2002 | Reed et al. | |
| 6,774,226 B1 * | 8/2004 | Jager et al. | 536/23.5 |
| 2003/0175715 A1 * | 9/2003 | Sun et al. | 435/6 |

FOREIGN PATENT DOCUMENTS

| | | | |
|---|---|---|---|
| WO | WO 98/33915 | | 6/1998 |
| WO | WO98/33915 | * | 8/1998 |
| WO | WO 00/06776 | | 2/2000 |
| WO | WO 00/55629 A3 | | 9/2000 |

OTHER PUBLICATIONS

Alberts, et al. Molecular Biology of the Cell, 3rd edition, 1994, p. 465.*
Putnam, ('Metastatic Cancer to the Lung'. In: Cancer, Principles and Practice of Oncology, DeVita et al, Eds, 1993, vol. 2, pp. 2678-2679)*
Garnett and Baldwin, "An Improved Synthesis of a Methotrexate-Albumin-791T/36 Monoclonal Antibody Conjugate Cytotoxic to Human Osteogenic Sarcoma Cell Lines[1]", Cancer Res. 1986 46:2407-2412.
Goodwin and Meares, "Pretargeting", Cancer Supplement 1997 80:2675-2680.
Griffin et al., "Initial Clinical Study of Indium-111-Labeled Clone 110 Anticarcinoembryonic Antigen Antibody in Patients With Colorectal Cancer", *J. Clin. Onc.* 1991 9(4):631-640.
Lauffer R.B., "Targeted Relaxation Enhancement Agents for MRI", *Magnetic Resonance in Medicine* 1991 22:339-342.
Pastan et al., "Immunotoxins", *Cell* 1986 47:641-648.
Rosenberg S. A. et al., "Use of Tumor-Infiltrating Lymphocytes and Interleukin-2 In The Immunotherapy of Patients with Metastatic Melanoma", *N. England J. Med.* 1988 319:1676-1680.
Sumerdon et al., "An Optimized Antibody-Chelator Conjugate for Imaging of Carcinoembryonic Antigen with Indium-111", *Nucl. Med. Biol.* 1990 17:247-254.
Sambrook et al., Molecular Cloning: A Laboratory Manual, 2nd Ed.; Cold Spring Harbor Laboratory Press, Cold Spring Harbor, N.Y. (1989).
Beaulieu M., et al., "Isolation and characterization of a Human Orphan UDP-Glucuronosyltransferase, UGT2B11", *Biochem. Biophys. Res. Comm.* 1998 248:44-50.
Database GenEmbl, Accession No. AF016492, Beaulieu et al. Direct Submission. Gene Sequence, Jul. 30, 1997.
Database GenEmbl, Accession No. AF183810, Momeni et al. Direct Submission. Gene Sequence, Sep. 6, 1999.
Momeni P., et al., Mutations in a new gene, encoding a zinc-finger protein, cause tricho-rhino-phalangeal syndrome type I. *Nature Genetics* Jan. 2000 24:71-74.
Janerich, D.T., "Material pattern of reproduction and risk of breast cancer in daughters:Results from the Utah population database", JNCI Nov. 1994 86(21) :1634-.
Abuladze N. et al., Molecular cloning, chromosomal localization, tissue distribution, and functional expression of the human pancreatic sodium bicarbonate cotransporter. J Biol Chem. Jul. 10, 1998; vol. 273(28):17689-95.
Abuladze N. et al., Structural organization of the human NBC1 gene: kNBC1 is transcribed from an alternative promoter in intron 3. Gene. Jun. 27, 2000; vol. 251(2):109-22.
Amlal H. et al., Characterization of Na+/HCO-3 cotransporter isoform NBC-3. Am J Physiol. Jun. 1999; vol. 276(6 Pt2):F903-13.
Burnham CE. et al., Cloning and functional expression of a human kidney Na+:HCO3-cotransporter. J Biol Chem. Aug. 1, 1997; vol. 272(31):19111-4.
Burnham CE. et al., Cloning, renal distribution, and regulation of the rat Na+-HCO3-cotransporter. Am J Physiol. Jun. 1998; vol. 274(6 Pt 2):F1119-26.
Choi I. et al., Cloning and characterization of a human electrogenic Na+-HCO-3 cotransporter isoform (hhNBC). Am J Physiol. Mar. 1999; vol. 276(3 Pt 1):C576-84.
Grichtchenko et al. Cloning, characterization, and chromosomal mapping for a human electroneutral $Na^+$-driven $CI-HCO_3$ Exchanger. J of Biol Chem. Mar. 16, 2001; vol. 276(11):8358-8363.
Ishibashi K. et al., Molecular cloning of a new sodium bicarbonate cotransporter cDNA from human retina. Biochem Biophys Res Commun. May 19, 1998; vol. 246(2):535-8.

(Continued)

*Primary Examiner*—Karen A. Canella
(74) *Attorney, Agent, or Firm*—Licata & Tyrrell P.C.; Nathan P. Letts

(57) ABSTRACT

Diagnostic markers for breast cancer referred to herein breast cancer specific genes or BCSGs are provided. Also provided are methods for using BCSGs to detect, diagnose, monitor, stage, prognosticate, image and treat breast cancer. Antibodies which specifically bind BCSGs and methods of using these antibodies to image and treat breast cancer are also provided.

50 Claims, No Drawings

OTHER PUBLICATIONS

Pushkin A, et al. Two C-terminal variants of NBC4, a new member of the sodium bicarbonate cotransporter family: cloning, characterization, and localization. IUBMB Life. Jul. 2000; vol. 50(1):13-9.

Pushkin A, et al., Cloning, characterization and chromosomal assignment of NBC4, a new member of the sodium bicarbonate cotransporter family.Biochim Biophys Acta. Sep. 7, 2000; vol. 1493(1-2):215-8.

Pushkin et al. Cloning, tissue distribution, genomic organization, and functional characterization of NBC3, a new member of the sodium bicarbonate cotransporter family. J of Biological Chem. Jun. 4, 1999; vol. 274(23):16569-16575.

Wang Z, et al., Mouse Na+:HCO3- cotransporter isoform NBC-3 (kNBC-3): cloning, expression, and renal distribution. Kidney International, 2001; vol. 59 (4):1405-14.

Database Genebank, Accession No. AAK26741, Pushkin et al., sodium bicarbonate cotransporter NBC4a [*Homo sapiens*], Mar. 28, 2001, see sequence.

Database Genebank, Accession No. AAG18492, Pushkin et al., sodium bicarbonate cotransoporter-like protein [ *Homo sapiens*], Oct. 4, 2000, see sequence.

Database Genebank, Accession No. AAC51645, Burnham et al sodium bicarbonate cotransporter [*Homo sapiens*], Jul. 26, 1997, see sequence.

Database Genebank, Accession No. AAC39840, Abuladze et al., pancreas sodium bicarbonate cotransporter [*Homo sapiens*], Jul. 9, 1998, see sequence.

Database Genebank, Accession No. AAD52981, Amlal et al., sodium bicarbonate cotransporter isoform 3 [*Homo sapiens*], Sep. 3, 1999, see sequence.

Database Genebank, Accession No. AAC82380, Grichtchenko et al., sodium bicarbonate cotransporter [*Homo sapiens*], Mar. 13, 2001, see sequence.

Database Genebank, Accession No. BAA25898, Ishibashi, sodium bicarbonate cotransprter2 [*Homo sapiens*], Mar. 28, 2001, see sequence.

Database Genebank, Accession No. AAD38322, Pushkin et al sodium bicarbonate cotransporter 3 [*Homo sapiens*], Jun. 12, 1999, see sequence.

Database Genebank, Accession No. AAD42020, Choi et al., sodium bicarbonate cotransporter [*Homo sapiens*] Jan. 31, 2000, see sequence.

Database Genebank, Accession No. AAF61705, wang et al., sodium bicarbonate cotransporter isoform 3 kNBC-3 [*Mus musculus*], Apr. 4, 2001, see sequence.

Database Genebank, Accession No. AAB83997, Burnham et al., sodium bicarbonate cotransporter [*Rattus norvegicus*], Nov. 8, 1997, see sequence.

Database Genebank, Accession No. AF243499, Pushkin et al., *Homo sapiens* sodium bicarbonate cotransporter NBC4a (NBC4) mRNA, complete cds, Mar. 28, 2001, see sequence.

Database Genebank, Accession No. AF207661, Pushkin et al *Homo sapiens* sodium bicarbonate cotransporter-like protein mRNA, partial cds, Oct. 4, 2000, see sequence.

Database Genebank, Accession No. AF007216, Burnham et al., *Homo sapiens* sodium bicarbonate cotransporter (HNBC1) mRNA, complete cds, Jul. 26, 1997, see sequence.

Database Genebank, Accession No. AF011390, Abuladze et al *Homo sapiens* pancreas sodium bicarbonate cotransporter mRNA, complete cds, Jul. 9, 1998, see sequence.

Database Genebank, Accession No. AF107099, Amlal et al., *Homo sapiens* sodium bicarbonate cotransporter isoform 3 (NBC-3) mRNA, partial cds, Sep. 3, 1999, see sequence.

Database Genebank, Accession No. AF069512, Grichtchenko et al., *Homo sapiens* sodium bicarbonate cotransporter (NBC) mRNA, complete cds, Mar. 13, 2001, see sequence.

Database Genebank, Accession No. AB012130, Ishibashi et al., *Homo sapiens* SBC2 mRNA for sodium bicarbonate cotransporter2, complete cds, May 1, 1998, see sequence.

Database Genebank, Accession No. AF047033, Pushkin et al., *Homo sapiens* sodium bicarbonate cotransporter 3 (SLC4A7) mRNA, complete cds, Jun. 12, 1999, see sequence.

Database Genebank, Accession No. AF069510, Choi et al., *Homo sapiens* sodium bicarbonate cotransporter (NBC) mRNA, complete cds, Jan. 31, 2000, see sequence.

Database Genebank, Accession No. AF224508, Wang et al., *Mus musculus* sodium bicarbonate cotransporter isoform 3 kNBC-3 mRNA, complete cds, Apr. 4, 2001, see sequence.

Database Genebank, Accession No. AF027362, Burnham et al., attus norvegicus sodium bicarbonate cotransporter (rNBC1) mRNA, complete cds, Nov. 8, 1997, see sequence.

Jin et al., "cDNA Cloning and Expression of Two New Members of the Human Liver UDP-Glucuronosyltransferase 2B Subfamily", Biochemical and Biophysical Research Communications 1993 194 (1) :496-503 XP-002121839.

Database Swissprot Accession No. P36537 Jun. 1, 1994 XP002267171.

\* cited by examiner

METHOD OF DIAGNOSING, MONITORING, STAGING, IMAGING AND TREATING BREAST CANCER

INTRODUCTION

This application claims the benefit of priority from U.S. provisional application Serial No. 60/166,973, filed Nov. 23, 1999.

FIELD OF THE INVENTION

This invention relates, in part, to newly identified breast cancer specific genes and assays for detecting, diagnosing, monitoring, staging, prognosticating, imaging and treating cancers, particularly breast cancer.

BACKGROUND OF THE INVENTION

It is estimated that one out of every nine women in America will develop breast cancer sometime during her life based on a lifespan of 85 years. Annually, over 180,000 women in the United States are diagnosed with breast cancer and approximately 46,000 die from this disease. Every woman is at risk for breast cancer. However, a woman's chances of developing breast cancer increase as she grows older; 80 percent of all cancers are found in women over the age of 50. There are also several risk factors that can increase a woman's chances of developing breast cancer. These include a family history of breast cancer, having no children or the first child after the age of 30, and an early start of menstruation. However, more than 70 percent of women who develop breast cancer have no known risk factors. Less than 10 percent of breast cancer cases are thought to be related to the BRCA1 gene discovered in 1994. Researchers are now investigating the role of other factors such as nutrition, alcohol, exercise, smoking, and oral contraceptives in development of this gynecologic cancer. Mammograms, or special x-rays of the breast, can detect more than 90 percent of all cancers.

Procedures used for detecting, diagnosing, monitoring, staging, and prognosticating breast cancer are of critical importance to the outcome of the patient. Patients diagnosed early generally have a much greater five-year survival rate as compared to the survival rate for patients diagnosed with distant metastasized breast cancer. New diagnostic methods which are more sensitive and specific for detecting early breast cancer are clearly needed.

Breast cancer patients are closely monitored following initial therapy and during adjuvant therapy to determine response to therapy and to detect persistent or recurrent disease or metastasis. Thus, there is also clearly a need for cancer markers which are more sensitive and specific in detecting breast cancer recurrence.

Another important step in managing breast cancer is to determine the stage of the patient's disease. Stage determination has potential prognostic value and provides criteria for designing optimal therapy. Generally, pathological staging of cancer is preferable over clinical staging because the former gives a more accurate prognosis. However, clinical staging would be preferred were it at least as accurate as pathological staging because it does not depend on an invasive procedure to obtain tissue for pathological evaluation. Staging of cancer would be improved by detecting new markers in cells, tissues or bodily fluids which could differentiate between different stages of invasion.

New breast cancer specific genes, refereed to herein as BCSGs, have now been identified for use in diagnosing, monitoring, staging, imaging and treating cancers, and in particular breast cancer. Accordingly, the present invention relates to new methods for detecting, diagnosing, monitoring, staging, prognosticating, in vivo imaging and treating cancer via a BCSG. BCSG refers, among other things, to native proteins expressed by the genes comprising the polynucleotide sequences of BCSG-1 or Gene ID 332369 (SEQ ID NO:1), BCSG-2 or Gene ID 480489 (SEQ ID NO:2 or 18), BCSG-3 or Gene ID 274731 (SEQ ID NO:3 or 20), BCSG-4 or Gene ID 173388 (SEQ ID NO:4) or BCSG-5 or Clone ID 3040232, Gene ID 411152 (SEQ ID NO:5). Exemplary proteins expressed by genes BCSG-2 and BCSG-3 are depicted herein as SEQ ID NO:19 and SEQ ID NO:21. By "BCSG" it is also meant herein variant polynucleotides which, due to degeneracy in genetic coding, comprise variations in nucleotide sequence as compared to SEQ ID NO:1, 2, 3, 4, 5, 18 or 20 but which still encode the same proteins. In the alternative, what is meant by BCSG as used herein, means the native mRNAs encoded by the genes comprising BCSG-1 or Gene ID 332369 (SEQ ID NO:1), BCSG-2 or Gene ID 480489 (SEQ ID NO:2 or 18), BCSG-3 or Gene ID 274731 (SEQ ID NO:3 or 20), BCSG-4 or Gene ID 173388 (SEQ ID NO:4) or BCSG-5 or Clone ID 3040232, Gene ID 411152 (SEQ ID NO:5) or it can refer to the actual genes comprising BCSG-1 or Gene ID 332369 (SEQ ID NO:1), BCSG-2 or Gene ID 480489 (SEQ ID NO:2 or 18), BCSG-3 or Gene ID 274731 (SEQ ID NO:3 or 20), BCSG-4 or Gene ID 173388 (SEQ ID NO:4) or BCSG-5 or Clone ID 3040232, Gene ID 411152 (SEQ ID NO:5), or levels of polynucleotides which are capable of hybridizing under stringent conditions to the antisense sequences of SEQ ID NO:1, 2, 3, 4, 5, 18 or 20.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide BCSGs comprising a polynucleotide of SEQ ID NO:1, 2, 3, 4, 5, 18 or 20 or a variant thereof, a protein expressed by a polynucleotide of SEQ ID NO:1, 2, 3, 4, 5, 18 or 20 or variant thereof which expresses the protein; or a polynucleotide which is capable of hybridizing under stringent conditions to the antisense sequence of SEQ ID NO:1, 2, 3, 4, 5, 18 or 20.

Further provided is a method for diagnosing the presence of breast cancer by analyzing for changes in levels of BCSG in cells, tissues or bodily fluids compared with levels of BCSG in preferably the same cells, tissues, or bodily fluid type of a normal human control, wherein a change in levels of BCSG in the patient versus the normal human control is associated with breast cancer.

Further provided is a method of diagnosing metastatic breast cancer in a patient having breast cancer which is not known to have metastasized by identifying a human patient suspected of having breast cancer that has metastasized; analyzing a sample of cells, tissues, or bodily fluid from such patient for BCSG; comparing the BCSG levels in such cells, tissues, or bodily fluid with levels of BCSG in preferably the same cells, tissues, or bodily fluid type of a normal human control, wherein an increase in BCSG levels in the patient versus the normal human control is associated with breast cancer which has metastasized.

Also provided by the invention is a method of staging breast cancer in a human by identifying a human patient having breast cancer; analyzing a sample of cells, tissues, or bodily fluid from such patient for BCSG; comparing BCSG levels in such cells, tissues, or bodily fluid with levels of BCSG in preferably the same cells, tissues, or bodily fluid type of a normal human control, wherein an increase in BCSG levels in the patient versus the normal human control is associated with a cancer which is progressing and a decrease in the levels of BCSG is associated with a cancer which is regressing or in remission.

Further provided is a method of monitoring breast cancer in a human patient for the onset of metastasis. The method comprises identifying a human patient having breast cancer that is not known to have metastasized; periodically analyzing cells, tissues, or bodily fluid from such patient for BCSG; comparing the BCSG levels in such cells, tissues, or bodily fluid with levels of BCSG in preferably the same cells, tissues, or bodily fluid type of a normal human control, wherein an increase in BCSG levels in the patient versus the normal human control is associated with a cancer which has metastasized.

Further provided is a method of monitoring the change in stage of cancer in a human patient having breast cancer by looking at levels of BCSG in the human patient. The method comprises identifying a human patient having breast cancer; periodically analyzing cells, tissues, or bodily fluid from such patient for BCSG; comparing the BCSG levels in such cells, tissue, or bodily fluid with levels of BCSG in preferably the same cells, tissues, or bodily fluid type of a normal human control, wherein an increase in BCSG levels in the patient versus the normal human control is associated with breast cancer which is progressing and a decrease in the levels of BCSG is associated with breast cancer which is regressing or in remission.

Further provided are methods of designing new therapeutic agents targeted to BCSGs for use in imaging and treating cancer. For example, in one embodiment, therapeutic agents such as antibodies targeted against a BCSG or fragments of such antibodies can be used to treat, detect or image localization of a BCSG in a patient for the purpose of detecting or diagnosing a disease or condition. In this embodiment, an increase in the amount of labeled antibody detected as compared to normal tissue would be indicative of tumor metastases or growth. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. Therapeutics agents such as small molecule and antibodies or fragments thereof which decrease the concentration and/or activity of a BCSG can also be used in the treatment of diseases characterized by overexpression of BCSG. In these applications, the antibody can be used without or with derivatization to a cytotoxic agent such as a radioisotope, enzyme, toxin, drug or a prodrug.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays and methods, both quantitative and qualitative for detecting, diagnosing, monitoring, staging, prognosticating, in vivo imaging and treating breast cancer by comparing levels of breast cancer specific genes (BCSGs) with levels of BCSGs in a normal human control. BCSG refers, among other things, to native proteins expressed by the genes comprising the polynucleotide sequences of BCSG-1 or Gene ID 332369 (SEQ ID NO:1), BCSG-2 or Gene ID 480489 (SEQ ID NO:2 or 18), BCSG-3 or Gene ID 274731 (SEQ ID NO:3 or 20), BCSG-4 or Gene ID 173388 (SEQ ID NO:4) or BCSG-5 or Clone ID 3040232, Gene ID 411152 (SEQ ID NO:5). Exemplary proteins expressed by genes BCSG-2 and BCSG-3 are depicted herein as SEQ ID NO:19 and SEQ ID NO:21. The genes encoding these proteins (SEQ ID NO:18 and 20) as well as the proteins (SEQ ID NO:19 and 21) have been disclosed in GenBank as Accession No. AF016492.1 (SEQ ID NO:18), AAC27891.1 (SEQ ID NO:19), AF183819 (SEQ ID NO:20) and AAF23614.1 (SEQ ID NO:21). By "BCSG" it is also meant herein variant polynucleotides which, due to degeneracy in genetic coding, comprise variations in nucleotide sequence as compared to SEQ ID NO:1, 2, 3, 4, 5, 18 or 20 but which still encode the same proteins. The native protein being detected may be whole, a breakdown product, a complex of molecules or chemically modified. In the alternative, what is meant by BCSG as used herein, means the native mRNAs encoded by the genes comprising BCSG-1 or Gene ID 332369 (SEQ ID NO:1), BCSG-2 or Gene ID 480489 (SEQ ID NO:2 or 18), BCSG-3 or Gene ID 274731 (SEQ ID NO:3 or 20), BCSG-4 or Gene ID 173388 (SEQ ID NO:4) or BCSG-5 or Clone ID 3040232, Gene ID 411152 (SEQ ID NO:5) or it can refer to the actual genes comprising BCSG-1 or Gene ID 332369 (SEQ ID NO:1), BCSG-2 or Gene ID 480489 (SEQ ID NO:2 or 18), BCSG-3 or Gene ID 274731 (SEQ ID NO:3 or 20), BCSG-4 or Gene ID 173388 (SEQ ID NO:4) or BCSG-5 or Clone ID 3040232, Gene ID 411152 (SEQ ID NO:5) or levels of polynucleotides which are capable of hybridizing under stringent conditions to the antisense sequences of SEQ ID NO:1, 2, 3, 4, 5, 18 or 20. Such levels are preferably measured in at least one of, cells, tissues and/or bodily fluids, including determination of normal and abnormal levels. Thus, for instance, a diagnostic assay in accordance with the invention for diagnosing over-expression of a BCSG protein compared to normal control bodily fluids, cells, or tissue samples can be used to diagnose the presence of cancers, and in particular breast cancer. BCSGs may be measured alone in the methods of the invention, or, more preferably, in combination with other diagnostic markers for breast cancer including other BCSGs as described herein. Other breast cancer markers, in addition to BCSGs, useful in the present invention are known to those of skill in the art.

Diagnostic Assays

The present intention provides methods for diagnosing the presence of cancer, and in particular breast cancer, by analyzing for changes in levels of BCSG in cells, tissues or bodily fluids from a human patient compared with levels of BCSG in cells, tissues or bodily fluids of preferably the same type from a normal human control, wherein an increase in levels of BCSG in the patient versus the normal human control is associated with the presence of cancer.

Without limiting the instant invention, typically, for a quantitative diagnostic assay a positive result indicating the patient being tested has breast cancer is one in which cells, tissues, or bodily fluid levels of a cancer marker, such as BCSG, are at least two times higher, and most preferably are at least five times higher, than in preferably the same cells, tissues, or bodily fluid of a normal human control.

The present invention also provides a method of diagnosing metastatic cancer, and in particular metastatic breast cancer, in a patient having breast cancer which has not yet metastasized. In the method of the present invention, a human cancer patient suspected of having breast cancer which may have metastasized (but which was not previously known to have metastasized) is identified. This is accomplished by a variety of means known to those of skill in the art.

In the present invention, determining the presence of BCSG in cells, tissues, or bodily fluid, is particularly useful for discriminating between cancers which have not metastasized and cancers which have metastasized. Existing techniques have difficulty discriminating between breast cancer which has metastasized and breast cancer which has not metastasized. However, proper treatment selection is often dependent upon such knowledge.

In the present invention, one of the cancer marker levels measured in cells, tissues, or bodily fluid of a human patient is BCSG. Levels in the human patient are compared with levels of BCSG in preferably the same cells, tissue, or bodily fluid type of a normal human control. That is, if the cancer marker being observed is BCSG in serum, this level is preferably compared with the level of BCSG in serum of a normal human control. An increase in BCSG in the human patient versus the normal human control is associated with a cancer which has metastasized.

Without limiting the instant invention, typically, for a quantitative diagnostic assay a positive result indicating the cancer in the patient being tested or monitored has metastasized is one in which cells, tissues, or bodily fluid levels of a cancer marker, such as BCSG, are at least two times higher, and more preferably are at least five times higher, than in preferably the same cells, tissues, or bodily fluid of a normal human control.

Normal human control as used herein includes a human patient without cancer and/or non cancerous samples from the patient; in the methods for diagnosing metastasis or monitoring for metastasis, normal human control preferably includes samples from a human patient that is determined by reliable methods to have breast cancer which has not metastasized, such as samples from the same patient prior to metastasis.

Staging

The invention also provides a method of staging cancers in a human patient.

The method comprises identifying a human patient having breast cancer and analyzing a sample of cells, tissues, or bodily fluid from such patient for BCSG. The measured BCSG levels are then compared to levels of BCSG in preferably the same cells, tissues, or bodily fluid type of a normal human control, wherein an increase in BCSG levels in the human patient versus the normal human control is associated with breast cancer which is progressing and a decrease in the levels of BCSG is associated with breast cancer which is regressing or in remission.

Monitoring

Further provided is a method of monitoring breast cancer in a human patient for the onset of metastasis. The method comprises identifying a human patient having breast cancer that is not known to have metastasized; periodically analyzing cells, tissues, or bodily fluid from such patient for BCSG; and comparing the BCSG levels in such cells, tissue, or bodily fluid with levels of BCSG in preferably the same cells, tissues, or bodily fluid type of a normal human control, wherein an increase in BCSG levels in the patient versus the normal human control is associated with breast cancer which has metastasized.

Further providing by this invention is a method of monitoring the change in stage of breast cancer. The method comprises identifying a human patient having breast cancer; periodically analyzing cells, tissues, or bodily fluid from such patient for BCSG; and comparing the BCSG levels in such cells, tissue, or bodily fluid with levels of BCSG in preferably the same cells, tissues, or bodily fluid type of a normal human control, wherein an increase in BCSG levels in the patient versus the normal human control is associated with breast cancer which is progressing in stage and a decrease in the levels of BCSG is associated with breast cancer which is regressing in stage or in remission.

Monitoring such patients for onset of metastasis is periodic and preferably done on a quarterly basis. However, this may be performed more or less frequently depending on the cancer, the particular patient, and the stage of the cancer.

Prognostic Testing and Clinical Trial Monitoring

The methods described herein can further be utilized as prognostic assays to identify subjects having or at risk of developing a disease or disorder associated with increased levels of BCSG. The present invention provides a method in which a test sample is obtained from a human patient and BCSG is detected. The presence of higher BCSG levels as compared to normal human controls is diagnostic for the human patient being at risk for developing cancer, particularly breast cancer.

The effectiveness of therapeutic agents to decrease expression or activity of the BCSGs of the invention can also be monitored by analyzing levels of expression of the BCSGs in a human patient in clinical trials or in in vitro screening assays such as in human cells. In this way, the gene expression pattern can serve as a marker, indicative of the physiological response of the human patient, or cells as the case may be, to the agent being tested.

Detection of Genetic Lesions or Mutations

The methods of the present invention can also be used to detect genetic lesions or mutations in BCSG, thereby determining if a human with the genetic lesion is at risk for breast cancer or has breast cancer. Genetic lesions can be detected, for example, by ascertaining the existence of a deletion and/or addition and/or substitution of one or more nucleotides from the BCSGs of this invention, a chromosomal rearrangement of BCSG, aberrant modification of BCSG (such as of the methylation pattern of the genomic DNA), the presence of a non-wild type splicing pattern of a mRNA transcript of BCSG, allelic loss of BCSG, and/or inappropriate post-transactional modification of BCSG protein.

Methods to detect such lesions in the BCSG of this invention are known to those of skill in the art.

Assay Techniques

Assay techniques that can be used to determine levels of gene expression, such as BCSG of the present invention, in a sample derived from a human are well-known to those of skill in the art. Such assay methods include radioimmunoassays, reverse transcriptase PCR (RT-PCR) assays, immunohistochemistry assays, in situ hybridization assays, competitive-binding assays, Western Blot analyses, ELISA assays and proteomic approaches, two-dimensional gel electrophoresis (2D electrophoresis) and non-gel based approaches such as mass spectrometry or protein interaction profiling. Among these, ELISAs are frequently preferred to diagnose a gene's expressed protein in biological fluids.

An ELISA assay initially comprises preparing an antibody, if not readily available from a commercial source, specific to BCSG, preferably a monoclonal antibody. In addition a reporter antibody generally is prepared which binds specifically to BCSG. The reporter antibody is attached to a detectable reagent such as a radioactive, fluorescent or enzymatic reagent, for example horseradish peroxidase enzyme or alkaline phosphatase.

To carry out the ELISA, antibody specific to BCSG is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time BCSG binds to the specific antibody attached to the polystyrene dish. Unbound sample is washed out with buffer. A reporter antibody specifically directed to BCSG and linked to a detectable reagent such as horseradish peroxidase is placed in the dish resulting in binding of the reporter antibody to any monoclonal antibody bound to BCSG. Unattached reporter antibody is then washed out. Reagents for peroxidase activity, including a colorimetric substrate are then added to the dish. Immobilized peroxidase, linked to BCSG antibodies, produces a colored reaction product. The amount of color developed in a given time period is proportional to the amount of BCSG protein present in the sample. Quantitative results typically are obtained by reference to a standard curve.

A competition assay can also be employed wherein antibodies specific to BCSG are attached to a solid support and labeled BCSG and a sample derived from the patient or human control are passed over the solid support. The amount of label detected which is attached to the solid support can be correlated to a quantity of BCSG in the sample.

Using all or a portion of a nucleic acid sequence of a BCSG of the present invention as a hybridization probe, nucleic acid methods can also be used to detect BCSG mRNA as a marker for cancer, and in particular breast cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e., gridding) can be used to both detect the expression of and quantitate the level of expression of that gene. In this approach, a cDNA encoding a BCSG gene is fixed to a substrate. The substrate may be of any suitable type including but not limited to glass, nitrocellulose, nylon or plastic. At least a portion of the DNA encoding the BCSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety cells, bodily fluids and/or tissue extracts (homogenates or solubilized tissue) obtained from the patient including tissue biopsy and autopsy material. Bodily fluids useful in the present invention include blood, urine, saliva, or any other bodily secretion or derivative thereof. Blood can include whole blood, plasma, serum, or any derivative of blood.

In Vivo Targeting of BCSGs/Breast Cancer Therapy

Identification of BCSGs is also useful in the rational design of new therapeutics for imaging and treating cancers, and in particular breast cancer. For example, in one embodiment, antibodies which specifically bind to BCSGs can be raised and used in vivo in patients suspected of suffering from cancer. Antibodies which specifically bind a BCSG can be injected into a patient suspected of having cancer for diagnostic and/or therapeutic purposes. The preparation and use of antibodies for in vivo diagnosis is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies directed against BCSGs can be used in a similar manner. Labeled antibodies which specifically bind a BCSG can be injected into patients suspected of having breast cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Localization of the label permits determination of the spread of the cancer. The amount of label within an organ or tissue also allows determination of the presence or absence of cancer in that organ or tissue.

For patients diagnosed with cancer, and in particular breast cancer, injection of an antibody which specifically binds a BCSG can also have a therapeutic benefit. The antibody may exert its therapeutic effect alone. Alternatively, the antibody can be conjugated to a cytotoxic agent such as a drug, toxin or radionuclide to enhance its therapeutic effect. Drug monoclonal antibodies have been described in the art for example by Garnett and Baldwin, Cancer Research 1986 46:2407–2412. The use of toxins conjugated to monoclonal antibodies for the therapy of various cancers has also been described by Pastan et al. Cell 1986 47:641–648. Yttrium-90 labeled monoclonal antibodies have been described for maximization of dose delivered to the tumor while limiting toxicity to normal tissues (Goodwin and Meares Cancer Supplement 1997 80:2675–2680). Other cytotoxic radionuclides including, but not limited to Copper-67, Iodine-131 and Rhenium-186 can also be used for labeling of antibodies against BCSG.

Antibodies which can be used in these in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

Screening Assays

The present invention also provides methods for identifying modulators which bind to BCSG protein or have a modulatory effect on the expression or activity of BCSG protein. Modulators which decrease the expression or activity of BCSG protein are believed to be useful in treating breast cancer. Such screening assays are known to those of skill in the art and include, without limitation, cell-based assays and cell free assays.

Small molecules predicted via computer imaging to specifically bind to regions of BCSG can also be designed, synthesized and tested for use in the imaging and treatment of breast cancer. Further, libraries of molecules can be screened for potential anticancer agents by assessing the ability of the molecule to bind to the BCSGs identified herein. Molecules identified in the library as being capable of binding to BCSG are key candidates for further evaluation for use in the treatment of breast cancer. In a preferred embodiment, these molecules will downregulate expression and/or activity of BCSG in cells.

Adoptive Immunotherapy and Vaccines

Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category and investigators at the National Cancer Institute (NCI) have used autologous reinfusion of peripheral blood lymphocytes or tumor-infiltrating lymphocytes (TIL), T cell cultures from biopsies of subcutaneous lymph nodules, to treat several human cancers (Rosenberg, S. A., U.S. Pat. No. 4,690,914, issued Sep. 1, 1987; Rosenberg, S. A., et al., 1988, N. England J. Med. 319:1676–1680).

The present invention relates to compositions and methods of adoptive immunotherapy for the prevention and/or treatment of primary and metastatic breast cancer in humans using macrophages sensitized to the antigenic BCSG molecules, with or without non-covalent complexes of heat shock protein (hsp). Antigenicity or immunogenicity of the BCSG is readily confirmed by the ability of the BCSG protein or a fragment thereof to raise antibodies or educate naive effector cells, which in turn lyse target cells expressing the antigen (or epitope).

Cancer cells are, by definition, abnormal and contain proteins which should be recognized by the immune system as foreign since they are not present in normal tissues. However, the immune system often seems to ignore this abnormality and fails to attack tumors. The foreign BCSG proteins that are produced by the cancer cells can be used to reveal their presence. The BCSG is broken into short fragments, called tumor antigens, which are displayed on the surface of the cell. These tumor antigens are held or presented on the cell surface by molecules called MHC, of which there are two types: class I and II. Tumor antigens in association with MHC class I molecules are recognized by cytotoxic T cells while antigen-MHC class II complexes are recognized by a second subset of T cells called helper cells. These cells secrete cytokines which slow or stop tumor growth and help another type of white blood cell, B cells, to make antibodies against the tumor cells.

In adoptive immunotherapy, T cells or other antigen presenting cells (APCs) are stimulated outside the body (ex vivo), using the tumor specific BCSG antigen. The stimulated cells are then reinfused into the patient where they attack the cancerous cells. Research has shown that using both cytotoxic and helper T cells is far more effective than using either subset alone. Additionally, the BCSG antigen may be complexed with heat shock proteins to stimulate the APCs as described in U.S. Pat. No. 5,985,270.

The APCs can be selected from among those antigen presenting cells known in the art including, but not limited to, macrophages, dendritic cells, B lymphocytes, and a combination thereof, and are preferably macrophages. In a preferred use, wherein cells are autologous to the individual, autologous immune cells such as lymphocytes, macrophages or other APCs are used to circumvent the issue of whom to select as the donor of the immune cells for adoptive transfer. Another problem circumvented by use of autologous immune cells is graft versus host disease which can be fatal if unsuccessfully treated.

In adoptive immunotherapy with gene therapy, DNA of the BCSG can be introduced into effector cells similarly as in conventional gene therapy. This can enhance the cytotoxicity of the effective cells to tumor cells as they have been manipulated to produce the antigenic protein resulting in improvement of the adoptive immunotherapy.

BCSG antigens of this invention are also useful as components of breast cancer vaccines. The vaccine comprises an immunogenically stimulatory amount of an BCSG antigen. Immunogenically stimulatory amount refers to that amount of antigen that is able to invoke the desired immune response in the recipient for the amelioration, or treatment of breast cancer. Effective amounts may be determined empirically by standard procedures well known to those skilled in the art.

The BCSG antigen may be provided in any one of a number of vaccine formulations which are designed to induce the desired type of immune response, e.g., antibody and/or cell mediated. Such formulations are known in the art and include, but are not limited to, formulations such as those described in U.S. Pat. No. 5,585,103. Vaccine formulations of the present invention used to stimulate immune responses can also include pharmaceutically acceptable adjuvants.

EXAMPLES

The present invention is further described by the following examples. These examples are provided solely to illustrate the invention by reference to specific embodiments. These exemplifications, while illustrating certain specific aspects of the invention, do not portray the limitations or circumscribe the scope of the disclosed invention.

Example 1

Identification of BCSGs via CLASP

Identification of BCSGs (Breast Cancer Specific Genes) was carried out by a systematic analysis of data in the LIFESEQ Gold (LSGold) database available from Incyte Pharmaceuticals, Palo Alto, Calif. using the data mining Cancer Leads Automatic Search Package (CLASP) developed by diaDexus LLC, Santa Clara Calif.

The CLASP performs the following steps:
(1) Selection of highly expressed organ specific genes based on the abundance level of the corresponding EST in the targeted organ versus all the other organs.
(2) Analysis of the expression level of each highly expressed organ specific gene in normal, tumor tissue, disease tissue and tissue libraries associated with tumor or disease.
(3) Selection of the candidates wherein component ESTs are exclusively or more frequently found in tumor libraries.

The CLASP allows the identification of highly expressed organ and cancer specific genes. A final manual in depth evaluation is then performed to finalize the Organ Cancer Specific Genes (OCSGs) selection. Table 1 provides the BCSGs of the present invention identified using CLASP.

TABLE 1

| | BCSGs | | |
|---|---|---|---|
| BCSG | SEQ ID NO: | LSGold Clone ID | LSGold Gene ID |
| BCSG-1 | 1 | none | 332369 |
| BCSG-2 | 2 or 18 | none | 480489 |
| BCSG-3 | 3 or 20 | none | 274731 |
| BCSG-4 | 4 | none | 173388 |
| BCSG-5 | 5 | 3040232 | 411152 |

Example 2

Determination of mRNA Expression of BCSG-5

The mRNA expression level of BCSG, BCSG-5 (SEQ ID NO:5), Clone ID 3040232, Gene ID 411152), also referred to as MAM009, in different tissues was analyzed using Real-Time quantitative PCR. The results presented here for BCSG-5 support the usage of CLASP as a tool for identifying cancer diagnostic markers.

These experiments were carried out using standard techniques, which are well known and routines to those of skill in the art, except where otherwise described in detail. Routine molecular biology techniques were carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Real-Time quantitative PCR with fluorescent TAQMAN probes (internal fluorescent oligonucleotide probes labeled with a 5' reporter dye and a downstream, 3' quencher dye) is a quantitation detection system utilizing the 5'-3' nuclease activity of Taq DNA polymerase. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) was used as this endogenous control. To calcualte relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution, and the level of the target gene were determined for every sample in normal and cancer tissue. Total RNA was extracted from normal tissues, cancer tissues, and from cancers and the corresponding matched adjacent tissues. Subsequently, first strand cDNA was prepared with reverse transcriptase and the polymerase chain reaction was done using primers and TAQMAN probe specific to each target gene. The results were analyzed using the ABI PRISM 7700 Sequence Detector. The absolute numbers are relative levels of expression of the target gene in a particular tissue compared to the calibrator tissue.

Primers used for expression analysis include:
BCSG-5 forward:
ACCCCATTTAGCCTGCCAT (SEQ ID NO:6)
BCSG-5 reverse:
ATGGGAGTATCTCATCTGCTCTCA (SEQ ID NO:7)
Q-PCR probe:
TGTTTGTTCATTCTTCAATTCCAAGGCTTT (SEQ ID NO:8)

The absolute numbers depicted in Table 2 are relative levels of expression of BCSG-5 in 12 normal different tissues. All the values are compared to normal testis (calibrator). These RNA samples are commercially available pools, originated by pooling samples of a particular tissue from different individuals.

TABLE 2

Relative Levels of BCSG-5 Expression in Pooled Samples

| Tissue | NORMAL |
|---|---|
| Brain | 0.00 |
| Heart | 0.00 |
| Kidney | 0.00 |
| Liver | 0.00 |
| Lung | 0.00 |
| Mammary gland | 106.15 |
| Muscle | 0.00 |
| Prostate | 0.00 |
| Small Intestine | 0.00 |
| Testis | 1.00 |
| Thymus | 0.00 |
| Uterus | 0.00 |

The relative levels of expression in Table 2 show that BCSG-5 mRNA expression is detected in the pool of normal mammary gland and in testis but not in the other 10 normal tissue pools analyzed. The level of expression in mammary gland pools is more than 100 fold higher than in testis. These results demonstrate that BCSG-5 mRNA expression is highly specific for mammary gland tissue and is also found in testis. Expression in a male specific tissue is not relevant in detecting cancer in female specific tissues.

The absolute numbers in Table 2 were obtained analyzing pools of samples of a particular tissue from different individuals. They can not be compared to the absolute numbers originated from RNA obtained from tissue samples of a single individual in Table 3.

The absolute numbers depicted in Table 3 are relative levels of expression of BCSG-5 in 78 pairs of matching samples. All the values are compared to normal testis (calibrator). A matching pair is formed by mRNA from the cancer sample for a particular tissue and mRNA from the normal adjacent sample for that same tissue from the same individual. In addition, 2 unmatched cancer samples (from ovary) and 2 unmatched normal samples (from ovary) were also tested.

TABLE 3

Relative Levels of BCSG-5 Expression in Individual Samples

| Sample ID | Tissue | Cancer | Matching Normal Adjacent | Normal |
|---|---|---|---|---|
| MamS621 | Mammary Gland 1 | 60.37 | 0.00 | |
| MamS516 | Mammary Gland 2 | 1.97 | 1.09 | |
| MamS079 | Mammary Gland 3 | 2.31 | 2.74 | |
| Mam517 | Mammary Gland 4 | 3.42 | 2.71 | |
| Mam59X | Mammary Gland 5 | 0.47 | 9.56 | |
| MamS127 | Mammary Gland 6 | 0.00 | 2.22 | |
| MamB011X | Mammary Gland 7 | 2.52 | 25.28 | |
| Mam522 | Mammary Gland 8 | 109.66 | 2.67 | |
| Mam51DN | Mammary Gland 9 | 11.71 | 169.77 | |
| Mam19DN | Mammary Gland 10 | 369.64 | 28.24 | |
| MamS123 | Mammary Gland 11 | 0.10 | 1.21 | |
| MamS997 | Mammary Gland 12 | 8.80 | 2.29 | |
| Mam162X | Mammary Gland 13 | 7.67 | 1.08 | |
| Mam220 | Mammary Gland 14 | 11.50 | 53.60 | |
| Mam699F | Mammary Gland 15 | 0.52 | 3.48 | |
| Mam42DN | Mammary Gland 16 | 1.39 | 3.54 | |
| Mam76DN | Mammary Gland 17 | 300.03 | 84.71 | |
| MamS854 | Mammary Gland 18 | 2.77 | 2.64 | |
| MamS967 | Mammary Gland 19 | 892.68 | 4.46 | |
| Mam986 | Mammary Gland 20 | 14.40 | 19.27 | |
| MamS699 | Mammary Gland 21 | 2.24 | 1.43 | |
| Mam355 | Mammary Gland 22 | 223.37 | 0.00 | |
| MamA06X | Mammary Gland 23 | 1220.50 | 2.26 | |
| MamS570 | Mammary Gland 24 | 0.00 | 120.39 | |
| MamS918 | Mammary Gland 25 | 181.43 | 60.30 | |
| End12XA | Endometrium 1 | 0.00 | 0.00 | |
| End28XA | Endometrium 2 | 0.00 | 0.00 | |
| End3AX | Endometrium 3 | 0.00 | 0.00 | |
| End4XA | Endometrium 4 | 0.00 | 0.00 | |
| End5XA | Endometrium 5 | 0.00 | 0.00 | |
| End10479 | Endometrium 6 | 0.00 | 0.00 | |
| End65RA | Endometrium 7 | 0.00 | 0.00 | |
| End68X | Endometrium 8 | 0.00 | 0.00 | |
| CvxNKS18 | Cervix 1 | 0.00 | 0.00 | |
| CvxNKS54 | Cervix 2 | 0.00 | 0.00 | |
| CvxNK23 | Cervix 3 | 0.00 | 0.00 | |
| CvxNK24 | Cervix 4 | 0.00 | 0.00 | |
| CvxKS52 | Cervix 5 | 0.00 | 0.00 | |
| CvxKS83 | Cervix 6 | 0.00 | 0.00 | |
| Utr141XO | Uterus 1 | 0.00 | 0.00 | |
| Utr135XO | Uterus 2 | 0.00 | 0.00 | |
| Utr23XU | Uterus 3 | 0.00 | 0.00 | |
| Utr85XU | Uterus 4 | 0.00 | 0.00 | |
| LngC20X | Lung 1 | 0.00 | 0.00 | |
| LngSQ56 | Lung 2 | 0.00 | 0.00 | |
| Lng90X | Lung 3 | 0.00 | 0.00 | |
| LngAC11 | Lung 4 | 0.00 | 0.00 | |
| Pro101XB | Prostate 1 | 0.00 | 0.00 | |
| Pro23B | Prostate 2 | 0.00 | 0.00 | |
| Skn448S | Skin 1 | 0.00 | 0.00 | |
| Skn784S | Skin 2 | 0.00 | 0.00 | |
| ClnSG45 | Colon 1 | 0.00 | 0.00 | |
| ClnTX01 | Colon 2 | 0.00 | 0.00 | |
| ClnAS46 | Colon 3 | 0.00 | 0.00 | |
| ClnAS67 | Colon 4 | 0.00 | 0.00 | |
| BldTR17 | Bladder 1 | 0.00 | 0.00 | |
| Bld66X | Bladder 2 | 0.00 | 0.00 | |
| Kid11XD | Kidney 1 | 0.00 | 0.00 | |
| Kid5XD | Kidney 2 | 0.00 | 0.00 | |
| Kid109XD | Kidney 3 | 0.00 | 0.00 | |
| Liv532L | Liver 1 | 0.00 | 0.00 | |
| Liv175L | Liver 2 | 0.00 | 0.00 | |
| Liv187L | Liver 3 | 0.00 | 0.00 | |
| OvrG010 | Ovary 1 | 0.00 | 0.00 | |
| Ovr1005O | Ovary 2 | 0.00 | | |
| Ovr1028 | Ovary 3 | 0.00 | | |
| Ovr103X | Ovary 4 | 0.00 | 0.00 | |
| Ovr18GA | Ovary 5 | | | 0.00 |
| Ovr206I | Ovary 6 | | | 0.00 |
| Pan92X | Pancreas 1 | 0.00 | 0.00 | |
| PanC044 | Pancreas 2 | 0.00 | 0.00 | |
| SmIH89 | Small Intestine 1 | 0.00 | 0.00 | |
| SmI21XA | Small Intestine 2 | 0.00 | 0.00 | |
| Sto15S | Stomach 1 | 0.00 | 0.00 | |
| StoAC44 | Stomach 2 | 0.00 | 0.00 | |
| Sto288S | Stomach 3 | 0.00 | 0.00 | |
| Sto531S | Stomach 4 | 0.00 | 0.00 | |
| Thr644T | Thyroid 1 | 0.00 | 0.00 | |
| Thr145T | Thyroid 2 | 0.00 | 0.00 | |
| Thr939T | Thyroid 3 | 0.00 | 0.00 | |
| Tst39X | Testis 1 | 0.00 | 0.00 | |
| Tst663T | Testis 2 | 0.00 | 0.00 | |

0.00 = Negative

Among 160 samples in Table 3 representing 17 different tissues significant expression is seen only in mammary gland tissues. These results confirm the tissue specificity results obtained with normal samples shown in Table 2. Table 2 and Table 3 represent a combined total of 172 samples in 21 human tissue types. One hundred and twenty samples representing 20 different tissue types excluding mammary gland had no detectable level of BCSG-5 mRNA. Other than mammary gland, BCSG-5 is detected only in one tissue type (testis) and then only in the pooled tissue sample (Table 2) but not in the matched testis cancer samples (Table 3; testis 1 and 2).

Comparisons of the level of mRNA expression in breast cancer samples and the normal adjacent tissue from the same individuals are shown in Table 3. BCSG-5 is expressed at higher levels in 12 of 25 (48%) cancer samples (mammary gland 1, 2, 8, 10, 12, 13, 17, 19, 21, 22, 23 and 25) compared to normal adjacent tissue.

Altogether, the high level of tissue specificity, plus the mRNA overexpression in 48% of the mammary gland matching samples tested are indicative of BCSG-5, and more generally BCSGs selected by CLASP, being good diagnostic markers for breast cancer.

Example 3

Determination of mRNA Expression of BCSG-1

The mRNA expression level of BCSG, BCSG-1 (SEQ ID NO:1, Gene ID 332369), also referred to as MAM014 were also determined in accordance with methods as set forth in Example 2.

Real-Time quantitative PCR was done using the following primers:
BCSG-1 forward:
5' GCCCATTAGCACCCAGATAAT 3' (SEQ ID NO:9)
BCSG-2 reverse:
5' GCCAACCCTTCACCTAAGAAA 3' (SEQ ID NO:10)
Q-PCR probe
5' CTTCCCACTGTACAAAGATTTTCCAGGATG 3' (SEQ ID NO:11)

The absolute numbers depicted in Table 4 are relative levels of expression of BCSG-1 in 37 normal samples from 25 different tissues. All the values are compared to normal kidney (calibrator). These RNA samples are commercially available pools, originated by pooling samples of a particular tissue from different individuals; except for the blood samples that they are normal samples from a single individual.

TABLE 4

Relative Levels of BCSG-1 Expression in Pooled Samples

| Tissue | NORMAL |
| --- | --- |
| Adrenal Gland | 1.09 |
| Bladder | 0.05 |
| Brain | 24.00 |
| Cervix | 3.84 |
| Colon | 0.00 |
| Endometrium | 10.41 |
| Esophagus | 0.18 |
| Heart | 0.01 |
| Kidney | 1.00 |
| Liver | 0.02 |
| Lung | 4.35 |
| Mammary | 1.19 |
| Muscle | 0.09 |
| Ovary | 23.51 |
| Pancreas | 0.86 |
| Prostate | 7.75 |
| Rectum | 0.33 |
| Small Intestine | 0.85 |
| Spleen | 17.51 |
| Stomach | 2.42 |
| Testis | 111.04 |

TABLE 4-continued

Relative Levels of BCSG-1 Expression in Pooled Samples

| Tissue | NORMAL |
| --- | --- |
| Thymus | 9.95 |
| Trachea | 6.43 |
| Uterus | 0.68 |
| Blood 1 | 34.42 |
| Blood 2 | 0.00 |
| Blood 3 | 21.19 |
| Blood 4 | 25.19 |
| Blood 5 | 51.09 |
| Blood 6 | 1144.10 |
| Blood 7 | 59.10 |
| Blood 8 | 60.13 |
| Blood 9 | 37.53 |
| Blood 10 | 0.00 |
| Blood 11 | 15.30 |
| Blood 12 | 0.00 |
| Blood 13 | 0.00 |

The relative levels of expression in Table 4 show that BCSG-1 mRNA expression is detected in the pool of normal mammary gland as well as in the other normal tissue analyzed.

The absolute numbers in Table 5 were obtained analyzing pools of samples of a particular tissue from different individuals, except for the blood samples. They can not be compared to the absolute numbers originated from RNA obtained from tissue samples of a single individual in Table 5.

The absolute numbers depicted in Table 5 are relative levels of expression of BCSG-1 in 77 pairs of matching samples. All the values are compared to normal kidney (calibrator). A matching pair is formed by mRNA from the cancer sample for a particular tissue and mRNA from the normal adjacent sample for that same tissue from the same individual. In addition, 3 unmatched cancer samples (from ovary) and 3 unmatched normal samples (from ovary) were also tested.

TABLE 5

Relative Levels of BCSG-1 Expression in Individual Samples

| Sample ID | Tissue | Cancer | Matching Normal Adjacent | Normal |
| --- | --- | --- | --- | --- |
| MamS621 | Mammary Gland 1 | 7.48 | 0.00 | |
| MamS516 | Mammary Gland 2 | 0.90 | 0.00 | |
| Mam173M | Mammary Gland 3 | 3.96 | 0.00 | |
| Mam497M | Mammary Gland 4 | 9.71 | 0.00 | |
| MamS079 | Mammary Gland 5 | 1.72 | 0.00 | |
| Mam517 | Mammary Gland 6 | 8.88 | 3.35 | |
| Mam726M | Mammary Gland 7 | 3.04 | 0.00 | |
| Mam59X | Mammary Gland 8 | 7.01 | 15.73 | |
| MamS127 | Mammary Gland 9 | 24.59 | 0.00 | |
| MamB011X | Mammary Gland 10 | 8.43 | 1.14 | |
| MamS22 | Mammary Gland 11 | 14.55 | 0.00 | |
| Mam15DN | Mammary Gland 12 | 4.16 | 0.00 | |
| Mam51DN | Mammary Gland 13 | 32.90 | 3.11 | |
| Mam976M | Mammary Gland 14 | 6.17 | 0.00 | |
| Mam543M | Mammary Gland 15 | 34.42 | 0.32 | |
| Mam245M | Mammary Gland 16 | 10.82 | 0.00 | |
| MamS123 | Mammary Gland 17 | 0.37 | 0.00 | |
| MamS997 | Mammary Gland 18 | 0.56 | 0.00 | |
| Mam162X | Mammary Gland 19 | 6.09 | 0.52 | |
| Mam220 | Mammary Gland 20 | 2.08 | 0.58 | |
| Mam699F | Mammary Gland 21 | 6.75 | 6.36 | |
| Mam42DN | Mammary Gland 22 | 10.16 | 0.00 | |

TABLE 5-continued

Relative Levels of BCSG-1 Expression in Individual Samples

| Sample ID | Tissue | Cancer | Matching Normal Adjacent | Normal |
|---|---|---|---|---|
| Mam76DN | Mammary Gland 23 | 31.23 | 4.68 | |
| MamS854 | Mammary Gland 24 | 6.11 | 0.00 | |
| MamS967 | Mammary Gland 25 | 86.22 | 0.00 | |
| Mam986 | Mammary Gland 26 | 13.36 | 9.00 | |
| MamS699 | Mammary Gland 27 | 4.52 | 0.00 | |
| Mam355 | Mammary Gland 28 | 107.38 | 0.00 | |
| MamA06X | Mammary Gland 29 | 43.26 | 0.00 | |
| MamSS70 | Mammary Gland 30 | 68.36 | 64.22 | |
| MamS918 | Mammary Gland 31 | 2.49 | 0.86 | |
| Bld66X | Bladder | 0.00 | 3.24 | |
| ClnTX01 | Colon 1 | 0.55 | 0.00 | |
| ClnAS43 | Colon 2 | 1.11 | 0.00 | |
| ClnAS49 | Colon 3 | 0.69 | 0.60 | |
| ClnRS45 | Colon 4 | 0.00 | 0.00 | |
| CvxNK24 | Cervix 1 | 2.53 | 0.69 | |
| CvxNKS54 | Cervix 2 | 1.71 | 0.54 | |
| CvxNK23 | Cervix 3 | 0.34 | 0.00 | |
| CvxNKS81 | Cervix 4 | 0.00 | 0.00 | |
| End5XA | Endometrium 1 | 1.16 | 2.85 | |
| End8911 | Endometrium 2 | 2.62 | 1.65 | |
| End8963 | Endometrium 3 | 6.50 | 0.00 | |
| End28XA | Endometrium 4 | 1.75 | 1.33 | |
| End65RA | Endometrium 5 | 0.45 | 0.00 | |
| End12XA | Endometrium 6 | 34.80 | 3.55 | |
| End3AX | Endometrium 7 | 0.00 | 0.00 | |
| Kid11XD | Kidney 1 | 0.94 | 1.42 | |
| Kid124D | Kidney 2 | 1.35 | 0.00 | |
| Liv532L | Liver 1 | 0.33 | 0.00 | |
| Liv390L | Liver 2 | 0.66 | 0.00 | |
| LngSQ56 | Lung 1 | 0.00 | 0.00 | |
| Lng223L | Lung 2 | 0.20 | 0.00 | |
| LngLC71 | Lung 3 | 7.67 | 8.20 | |
| LngAC90 | Lung 4 | 11.70 | 0.98 | |
| Lng75XC | Lung 5 | 0.00 | 0.00 | |
| OvrA082 | Ovary 1 | 21.33 | 42.96 | |
| OvrA082 | Ovary 2 | 52.68 | 186.62 | |
| Ovr103X | Ovary 3 | 44.88 | 17.67 | |
| Ovr1005O | Ovary 4 | 6.89 | | |
| Ovr1028 | Ovary 5 | 0.44 | | |
| Ovr1040O | Ovary 6 | 0.80 | | |
| Ovr18GA | Ovary 7 | | | 6.63 |
| Ovr206I | Ovary 8 | | | 1.46 |
| Ovr20GA | Ovary 9 | | | 5.96 |
| Pan92X | Pancreas 1 | 0.00 | 0.00 | |
| Pan77X | Pancreas 2 | 0.24 | 0.00 | |
| Pro23B | Prostate 1 | 0.80 | 0.00 | |
| Pro13XB | Prostate 2 | 0.05 | 17.75 | |
| Skn448S | Skin 1 | 0.00 | 0.00 | |
| Skn784S | Skin 2 | 0.13 | 0.11 | |
| SmIntH89 | Small Intestine 1 | 0.00 | 0.00 | |
| Sto264S | Stomach 1 | 0.80 | 1.15 | |
| Sto15S | Stomach 2 | 0.23 | 2.29 | |
| Sto27S | Stomach 3 | 1.07 | 1.35 | |
| Thr644T | Thyroid 1 | 0.00 | 0.00 | |
| Thr143T | Thyroid 2 | 0.58 | 0.00 | |
| Tst663T | Testis 1 | 5.46 | 1.80 | |
| Tst647T | Testis 2 | 1.27 | 5.68 | |
| Utr23XU | Uterus 1 | 9.38 | 1.17 | |
| Utr85XU | Uterus 2 | 4.36 | 2.17 | |
| Utr141XO | Uterus 3 | 0.00 | 0.00 | |
| Utr135XO | Uterus 4 | 7.53 | 10.10 | |

0.00 = Negative

Table 5 represents 160 samples in 17 different tissues. Table 4 and Table 5 represent a combined total of 197 samples in 27 human tissue types. Comparisons of the level of mRNA expression in breast cancer samples and the normal adjacent tissue from the same individuals are shown in Table 5. BCSG-1 is expressed at higher levels in 27 of 30 (90%) cancer samples (mammary gland 1–7, 9–20, 22–25, 27–29, and 31) compared to normal adjacent tissue.

Example 4

Determination of mRNA Expression of BCSG-2

The mRNA expression level of BCSG, BCSG-2 (SEQ ID NO:2 or 18, Gene ID 480489), also referred to as MAM013 were also determined in accordance with methods as set forth in Example 2.

Real-Time quantitative PCR was done using the following primers:

BCSG-2 forward:
5' CCTGGAGTTTTCAATTTCCTCA 3' (SEQ ID NO:12)
BCSG-2 reverse:
5' CCCCAGAGAAAACACCACAA 3' (SEQ ID NO:13)
Q-PCR probe
5' ACTCCTCCATTTCCTTAGGTAGGGGTTTG 3' (SEQ ID NO:14)

The absolute numbers depicted in Table 6 are relative levels of expression of BCSG-2 in 37 normal samples from 25 different tissues. All the values are compared to normal liver (calibrator). These RNA samples are commercially available pools, originated by pooling samples of a particular tissue from different individuals, except for the blood samples that they are normal samples from a single individual.

TABLE 6

Relative Levels of BCSG-2 Expression in Pooled Samples

| Tissue | NORMAL |
|---|---|
| Adrenal Gland | 0.00 |
| Bladder | 0.00 |
| Brain | 0.00 |
| Cervix | 0.00 |
| Colon | 0.00 |
| Endometrium | 0.33 |
| Esophagus | 0.00 |
| Heart | 0.02 |
| Kidney | 0.28 |
| Liver | 1.00 |
| Lung | 0.07 |
| Mammary | 20.39 |
| Muscle | 0.00 |
| Ovary | 0.00 |
| Pancreas | 0.05 |
| Prostate | 0.26 |
| Rectum | 0.00 |
| Small Intestine | 0.00 |
| Spleen | 0.00 |
| Stomach | 0.12 |
| Testis | 1.55 |
| Thymus | 0.55 |
| Trachea | 1.23 |
| Uterus | 0.00 |
| Blood 1 | 0.00 |
| Blood 2 | 0.00 |
| Blood 3 | 0.00 |
| Blood 4 | 0.00 |
| Blood 5 | 6.17 |
| Blood 6 | 0.00 |
| Blood 7 | 0.00 |
| Blood 8 | 0.00 |
| Blood 9 | 16.97 |
| Blood 10 | 0.00 |
| Blood 11 | 77.98 |
| Blood 12 | 0.00 |
| Blood 13 | 0.00 |

The relative levels of expression in Table 6 show that BCSG-2 mRNA expression is detected in the pool of normal mammary gland. The level of expression is higher than in the other tissues with the exception of two blood samples.

The absolute numbers in Table 6 were obtained analyzing pools of samples of a particular tissue from different individuals, except for the blood samples. They can not be compared to the absolute numbers originated from RNA obtained from tissue samples of a single individual in Table 7.

The absolute numbers depicted in Table 7 are relative levels of expression of BCSG-2 in 76 pairs of matching samples. All the values are compared to normal liver (calibrator). A matching pair is formed by mRNA from the cancer sample for a particular tissue and mRNA from the normal adjacent sample for that same tissue from the same individual. In addition, 3 unmatched cancer samples (from ovary) and 3 unmatched normal samples (from ovary) were also tested.

TABLE 7

Relative Levels of BCSG-2 Expression in Individual Samples

| Sample ID | Tissue | Cancer | Matching Normal Adjacent | Normal |
|---|---|---|---|---|
| MamS621 | Mammary Gland 1 | 0.00 | 0.00 | |
| Mam173M | Mammary Gland 2 | 7.21 | 0.00 | |
| Mam497M | Mammary Gland 3 | 1634.92 | 31.12 | |
| MamS079 | Mammary Gland 4 | 42.56 | 1.39 | |
| Mam517 | Mammary Gland 5 | 2.42 | 4.21 | |
| Mam726M | Mammary Gland 6 | 0.00 | 6.75 | |
| Mam59X | Mammary Gland 7 | 0.00 | 16.11 | |
| MamS127 | Mammary Gland 8 | 5.31 | 0.00 | |
| MamB001X | Mammary Gland 9 | 0.87 | 182.28 | |
| Mam522 | Mammary Gland 10 | 480.47 | 0.18 | |
| Mam19DN | Mammary Gland 11 | 4.79 | 0.22 | |
| Mam51DN | Mammary Gland 12 | 19.49 | 72.76 | |
| Mam976M | Mammary Gland 13 | 62.25 | 0.00 | |
| Mam543M | Mammary Gland 14 | 103.97 | 0.00 | |
| Mam245M | Mammary Gland 15 | 49.01 | 615.24 | |
| MamS123 | Mammary Gland 16 | 0.42 | 1.27 | |
| MamS997 | Mammary Gland 17 | 0.24 | 0.66 | |
| Mam162X | Mammary Gland 18 | 0.45 | 1.39 | |
| Mam220 | Mammary Gland 19 | 0.00 | 0.00 | |
| Mam699F | Mammary Gland 20 | 0.00 | 12.38 | |
| Mam42DN | Mammary Gland 21 | 44.48 | 11.47 | |
| Mam76DN | Mammary Gland 22 | 9.32 | 26.26 | |
| MamS854 | Mammary Gland 23 | 6.50 | 103.61 | |
| MamS967 | Mammary Gland 24 | 3.36 | 5.13 | |
| Mam986 | Mammary Gland 25 | 7.67 | 65.12 | |
| MamS699 | Mammary Gland 26 | 1.68 | 11.63 | |
| Mam355 | Mammary Gland 27 | 1.32 | 0.00 | |
| MamA06X | Mammary Gland 28 | 1.73 | 0.26 | |
| MamS570 | Mammary Gland 29 | 0.00 | 194.69 | |
| MamS918 | Mammary Gland 30 | 0.07 | 0.13 | |
| Bld66X | Bladder | 0.00 | 0.00 | |
| ClnTX01 | Colon 1 | 0.00 | 0.00 | |
| ClnAS43 | Colon 2 | 0.00 | 0.00 | |
| ClnAS49 | Colon 3 | 0.00 | 0.00 | |
| ClnRS45 | Colon 4 | 0.00 | 0.01 | |
| CvxNK24 | Cervix 1 | 0.00 | 0.00 | |
| CvxNKS54 | Cervix 2 | 0.00 | 0.00 | |
| CvxNK23 | Cervix 3 | 0.02 | 0.00 | |
| CvxNKS81 | Cervix 4 | 0.00 | 0.00 | |
| End5XA | Endometrium 1 | 0.00 | 0.00 | |
| End8911 | Endometrium 2 | 0.00 | 0.00 | |
| End8963 | Endometrium 3 | 0.00 | 0.00 | |
| End28XA | Endometrium 4 | 0.05 | 0.00 | |
| End65RA | Endometrium 5 | 0.00 | 0.00 | |
| End12XA | Endometrium 6 | 0.23 | 0.00 | |
| End3AX | Endometrium 7 | 0.00 | 0.05 | |
| Kid11XD | Kidney 1 | 0.04 | 0.00 | |
| Kid124D | Kidney 2 | 0.37 | 0.00 | |
| Liv532L | Liver 1 | 0.00 | 2.02 | |
| Liv390L | Liver 2 | 0.08 | 0.56 | |
| Lng223L | Lung 1 | 0.00 | 0.00 | |
| LngLC71 | Lung 2 | 0.00 | 0.00 | |
| LngSQ56 | Lung 3 | 0.00 | 0.00 | |
| LngAC90 | Lung 4 | 0.00 | 0.00 | |
| Lng75XC | Lung 5 | 0.00 | 0.00 | |
| OvrA082 | Ovary 1 | 0.00 | 0.00 | |
| OvrA082 | Ovary 2 | 0.00 | 0.00 | |
| Ovr103X | Ovary 3 | 0.07 | 0.00 | |
| Ovr1005O | Ovary 4 | 1.09 | | |
| Ovr1028 | Ovary 5 | 0.00 | | |
| Ovr1040O | Ovary 6 | 0.00 | | |
| Ovr18GA | Ovary 7 | | | 0.00 |
| Ovr206I | Ovary 8 | | | 0.00 |
| Ovr20GA | Ovary 9 | | | 0.00 |
| Pan92X | Pancreas 1 | 0.00 | 0.00 | |
| Pan77X | Pancreas 2 | 1.91 | 1.11 | |
| Pro23B | Prostate 1 | 0.01 | 0.00 | |
| Pro13XB | Prostate 2 | 0.00 | 0.00 | |
| Skn448S | Skin 1 | 0.00 | 0.00 | |
| Skn784S | Skin 2 | 0.00 | 0.00 | |
| SmIntH89 | Small Intestine 1 | 0.00 | 0.02 | |
| Sto264S | Stomach 1 | 0.00 | 0.00 | |
| Sto15S | Stomach 2 | 0.04 | 0.00 | |
| Sto27S | Stomach 3 | 0.00 | 0.00 | |
| Thr644T | Thyroid 1 | 0.00 | 0.12 | |
| Thr143T | Thyroid 2 | 0.03 | 3.73 | |
| Tst663T | Testis 1 | 0.09 | 0.00 | |
| Tst647T | Testis 2 | 0.55 | 0.00 | |
| Utr23XU | Uterus 1 | 0.00 | 0.00 | |
| Utr85XU | Uterus 2 | 0.00 | 2.85 | |
| Utr141XO | Uterus 3 | 0.04 | 0.00 | |
| Utr135XO | Uterus 4 | 0.17 | 0.12 | |

0.00 = Negative

Table 7 represents 158 samples in 17 different tissues. Table 6 and Table 7 represent a combined total of 195 samples in 25 human tissue types. Comparisons of the level of mRNA expression in breast cancer samples and the normal adjacent tissue from the same individuals are shown in Table 7. BCSG-2 is expressed at higher levels in 11 of 30 (37%) cancer samples (mammary gland 2–4, 8, 10, 11, 13, 14, 21, 27, 28) compared to normal adjacent tissue.

Example 5

Determination of mRNA Expression of BCSG-3

The mRNA expression level of BCSG, BCSG-3 (SEQ ID NO:3 or 20, Gene ID 274731), also referred to as MAM017 were also determined in accordance with methods as set forth in Example 2.

Real-Time quantitative PCR was done using the following primers:
BCSG-3 forward:
5' GAGCACTTCCTTTTGGTTTTTC 3' (SEQ ID NO:15)
BCSG-3 reverse:
5' GCCCTAGCATATTCCAGAAGTTC 3' (SEQ ID NO:16)
Q-PCR probe
5' TAGACAGTGGGCTCACATGTTCCTGATAGTG 3' (SEQ ID NO:17)

The absolute numbers depicted in Table 8 are relative levels of expression of BCSG-3 in 36 normal samples from 25 different tissues. All the values are compared to normal prostate (calibrator). These RNA samples are commercially available pools, originated by pooling samples of a particular tissue from different individuals, except for the blood samples that they are normal samples from a single individual.

TABLE 8

Relative Levels of BCSG-3 Expression in Pooled Samples

| Tissue | NORMAL |
|---|---|
| Adrenal Gland | 0.16 |
| Bladder | 0.02 |
| Brain | 0.12 |
| Cervix | 1.41 |
| Colon | 0.01 |
| Endometrium | 3.77 |
| Esophagus | 0.03 |
| Heart | 0.02 |
| Kidney | 0.07 |
| Liver | 0.00 |
| Lung | 0.59 |
| Mammary | 7.67 |
| Muscle | 0.08 |
| Ovary | 0.94 |
| Pancreas | 0.14 |
| Prostate | 1.00 |
| Rectum | 0.13 |
| Small Intestine | 0.05 |
| Spleen | 0.89 |
| Stomach | 0.17 |
| Testis | 0.20 |
| Thymus | 0.56 |
| Trachea | 0.39 |
| Uterus | 1.22 |
| Blood 1 | 1.91 |
| Blood 2 | 1.76 |
| Blood 3 | 0.76 |
| Blood 4 | 0.18 |
| Blood 5 | 1.41 |
| Blood 6 | 1.54 |
| Blood 7 | 0.48 |
| Blood 8 | 1.92 |
| Blood 9 | 1.63 |
| Blood 10 | 1.65 |
| Blood 11 | 1.83 |
| Blood 12 | 0.37 |

The relative levels of expression in Table 8 show that BCSG-3 mRNA expression is detected in the pool of normal mammary gland with the highest expression value.

The absolute numbers in Table 8 were obtained analyzing pools of samples of a particular tissue from different individuals, except for the blood samples. They can not be compared to the absolute numbers originated from RNA obtained from tissue samples of a single individual in Table 9.

The absolute numbers depicted in Table 9 are relative levels of expression of BCSG-3 in 68 pairs of matching samples. All the values are compared to normal prostate (calibrator). A matching pair is formed by mRNA from the cancer sample for a particular tissue and mRNA from the normal adjacent sample for that same tissue from the same individual. In addition, 1 unmatched cancer sample (from ovary) and 1 unmatched normal sample (from ovary) were also tested.

TABLE 9

Relative Levels of BCSG-3 Expression in Individual Samples

| Sample ID | Tissue | Cancer | Matching Normal Adjacent | Normal |
|---|---|---|---|---|
| Mam497M | Mammary Gland 1 | 3.22 | 1.11 | |
| Mam173M | Mammary Gland 2 | 1.39 | 17.75 | |
| Mam726M | Mammary Gland 3 | 7.62 | 1.31 | |
| MamS516 | Mammary Gland 4 | 11.08 | 0.10 | |
| MamS621 | Mammary Gland 5 | 18.25 | 0.05 | |
| MamS079 | Mammary Gland 6 | 0.78 | 0.24 | |
| Mam19DN | Mammary Gland 7 | 71.01 | 1.39 | |
| Mam522 | Mammary Gland 8 | 3.35 | 0.16 | |
| MamS127 | Mammary Gland 9 | 48.00 | 0.48 | |
| Mam162X | Mammary Gland 10 | 0.18 | 0.65 | |
| MamS123 | Mammary Gland 11 | 49.69 | 0.00 | |
| MamS997 | Mammary Gland 12 | 141.53 | 0.48 | |
| Mam543M | Mammary Gland 13 | 34.66 | 0.10 | |
| Mam976M | Mammary Gland 14 | 0.37 | 0.10 | |
| Mam74DN | Mammary Gland 15 | 35.14 | 4.36 | |
| MamS918 | Mammary Gland 16 | 16.74 | 5.58 | |
| MamS854 | Mammary Gland 17 | 1.11 | 1.58 | |
| Mam986 | Mammary Gland 18 | 0.58 | 1.14 | |
| MamS967 | Mammary Gland 19 | 121.94 | 2.97 | |
| Mam355 | Mammary Gland 20 | 11.35 | 0.06 | |
| MamA06X | Mammary Gland 21 | 7.65 | 0.13 | |
| Bld32XK | Bladder 1 | 0.17 | 0.02 | |
| Bld66X | Bladder 2 | 0.17 | 0.13 | |
| BldTR17 | Bladder 3 | 6.21 | 0.00 | |
| Bld46XK | Bladder 4 | 0.06 | 0.00 | |
| BldTR14 | Bladder 5 | 0.79 | 0.19 | |
| ClnB56 | Colon 1 | 0.12 | 0.10 | |
| ClnDC63 | Colon 2 | 0.21 | 1.09 | |
| CvxKS52 | Cervix 1 | 10.74 | 2.21 | |
| CvxNK24 | Cervix 2 | 6.96 | 4.63 | |
| CvxKS83 | Cervix 3 | 2.29 | 2.23 | |
| CvxNK23 | Cervix 4 | 0.22 | 1.54 | |
| End10479 | Endometrium 1 | 4.68 | 5.13 | |
| End12XA | Endometrium 2 | 1.68 | 2.00 | |
| End5XA | Endometrium 3 | 0.38 | 0.40 | |
| End65RA | Endometrium 4 | 0.49 | 0.38 | |
| End28XA | Endometrium 5 | 4.32 | 2.94 | |
| End3AX | Endometrium 6 | 0.21 | 0.21 | |
| Kid6XD | Kidney 1 | 0.06 | 0.16 | |
| Kid710K | Kidney 2 | 0.03 | 0.10 | |
| Liv175L | Liver 1 | 1.24 | 0.09 | |
| Liv187L | Liver 2 | 0.07 | 0.06 | |
| Liv15XA | Liver 3 | 0.02 | 0.01 | |
| Lng47XQ | Lung 1 | 0.15 | 0.06 | |
| LngAC88 | Lung 2 | 1.78 | 0.95 | |
| LngAC90 | Lung 3 | 0.46 | 0.00 | |
| LngSQ80 | Lung 4 | 1.91 | 0.35 | |
| Ovr103X | Ovary 1 | 25.63 | 2.52 | |
| OvrA084 | Ovary 2 | 7.70 | 3.19 | |
| OvrG010 | Ovary 3 | 0.62 | 3.40 | |
| OvrG021 | Ovary 4 | 0.09 | 0.45 | |
| Ovr1118 | Ovary 5 | 0.13 | | |
| Ovr32RA | Ovary 6 | | | 2.81 |
| Pan77X | Pancreas 1 | 0.56 | 0.19 | |
| Pan82XP | Pancreas 2 | 0.62 | 0.73 | |
| Pro109XB | Prostate 1 | 0.00 | 0.10 | |
| Pro125XB | Prostate 2 | 0.05 | 0.01 | |
| Skn248S | Skin 1 | 0.94 | 0.02 | |
| Skn287S | Skin 2 | 0.36 | 0.05 | |
| SmIntH89 | Small Intestine 1 | 0.12 | 0.04 | |
| SmInt21XA | Small Intestine 2 | 0.29 | 0.01 | |
| Sto115S | Stomach 1 | 1.17 | 0.44 | |
| Sto15S | Stomach 2 | 0.15 | 0.18 | |
| StoMT54 | Stomach 3 | 0.12 | 0.18 | |
| Thr590D | Thyroid | 3.46 | 3.33 | |
| Tst647T | Testis | 1.06 | 0.24 | |
| Utr141XO | Uterus 1 | 2.86 | 0.51 | |
| Utr23XU | Uterus 2 | 0.60 | 0.13 | |
| Utr85XU | Uterus 3 | 12.21 | 1.43 | |
| Utr135XO | Uterus 4 | 2.98 | 2.93 | |

0.00 = Negative

Table 9 represents 138 samples in 17 different tissues. Table 8 and Table 9 represent a combined total of 174 samples in 26 human tissue types.

Comparisons of the level of mRNA expression in breast cancer samples and the normal adjacent tissue from the same individuals are shown in Table 8. BSCG-3 is expressed at higher levels in 17 of 21 (81%) cancer samples (mammary gland 1, 3–6, 7–9, 11–16, 19–21) compared to normal adjacent tissue.

What is claimed is:

1. A method for diagnosing the presence of breast cancer in a patient comprising:
   (a) determining levels of Breast Cancer Specific Gene (BCSG) polynucleotide in cells, tissues or whole blood in a patient; and
   (b) comparing the determined levels of BCSG polynucleotide with levels of BCSG polynucleotide in cells, tissues or whole blood from a normal human control, wherein an increase in determined levels of BCSG polynucleotide in said patient versus normal human control is associated with the presence of breast cancer and wherein the BCSG polynucleotide comprises SEQ ID NO:1 or 2.

2. A method of diagnosing metastases of breast cancer in a patient comprising:
   (a) identifying a patient having breast cancer that is not known to have metastasized;
   (b) determining Breast Cancer Specific Gene (BCSG) polynucleotide levels in cells, tissues, or whole blood from said patient; and
   (c) comparing the determined BCSG polynucleotide levels with levels of BCSG polynucleotide in cells, tissue, or whole blood of a normal human control, wherein an increase in determined BCSG polynucleotide levels in the patient versus the normal human control is associated with breast cancer which has metastasized and wherein the BCSG polynucleotide comprises SEQ ID NO:1 or 2.

3. A method of staging breast cancer in a patient having breast cancer comprising:
   (a) identifying a patient having breast cancer;
   (b) determining Breast Cancer Specific Gene (BCSG) polynucleotide levels in a sample of cells, tissue, or whole blood from said patient; and
   (c) comparing determined BCSG polynucleotide levels with levels of BCSG polynucleotide in cells, tissues, or whole blood of a normal human control, wherein an increase in determined BCSG polynucleotide levels in said patient versus the normal human control is associated with breast cancer which is progressing and a decrease in the determined BCSG polynucleotide levels is associated with breast cancer which is regressing or in remission and wherein the BCSG polynucleotide comprises SEQ ID NO:1 or 2.

4. A method of monitoring breast cancer in a patient for the onset of metastasis comprising:
   (a) identifying a patient having breast cancer that is not known to have metastasized;
   (b) periodically determining levels of Breast Cancer Specific Gene (BCSG) polynucleotide in samples of cells, tissues, or whole blood from said patient; and
   (c) comparing the periodically determined BCSG polynucleotide levels with levels of BCSG polynucleotide in cells, tissues, or whole blood of a normal human control, wherein an increase in any one of the periodically determined BCSG polynucleotide levels in the patient versus the normal human control is associated with breast cancer which has metastasized and wherein the BCSG polynucleotide comprises SEQ ID NO:1 or 2.

5. A method of monitoring a change in stage of breast cancer in a patient comprising:
   (a) identifying a patient having breast cancer;
   (b) periodically determining levels of Breast Cancer Specific Genes (BCSG) polynucleotide in cells, tissues, or whole blood from said patient; and
   (c) comparing the periodically determined BCSG polynucleotide levels with levels of BCSG polynucleotide in cells, tissues, or whole blood of a normal human control, wherein an increase in any one of the periodically determined BCSG polynucleotide levels in the patient versus the normal human control is associated with breast cancer which is progressing in stage and a decrease is associated with breast cancer which is regressing in stage or in remission and wherein the BCSG polynucleotide comprises SEQ ID NO:1 or 2.

6. The method of claim 1 wherein the BCSG polynucleotide comprises SEQ ID NO:1.

7. The method of claim 1 wherein the BCSG polynucleotide comprises SEQ ID NO:2.

8. The method of claim 2 wherein the BCSG polynucleotide comprises SEQ ID NO:1.

9. The method of claim 2 wherein the BCSG polynucleotide comprises SEQ ID NO:2.

10. The method of claim 3 wherein the BCSG polynucleotide comprises SEQ ID NO:1.

11. The method of claim 3 wherein the BCSG polynucleotide comprises SEQ ID NO:2.

12. The method of claim 4 wherein the BCSG polynucleotide comprises SEQ ID NO:1.

13. The method of claim 4 wherein the BCSG polynucleotide comprises SEQ ID NO:2.

14. The method of claim 5 wherein the BCSG polynucleotide comprises SEQ ID NO:1.

15. The method of claim 5 wherein the BCSG polynucleotide comprises SEQ ID NO:2.

16. A method for diagnosing the presence of breast cancer in a patient comprising:
- (a) determining levels of Breast Cancer Specific Gene (BCSG) polynucleotide in cells, tissues or whole blood in a patient; and
- (b) comparing the determined levels of BCSG polynucleotide with levels of BCSG polynucleotide in cells, tissues or whole blood from a normal human control, wherein an increase in determined levels of BCSG polynucleotide in said patient versus normal human control is associated with the presence of breast cancer and wherein the BCSG polynucleotide comprises SEQ ID NO:18.

17. A method of diagnosing metastases of breast cancer in a patient comprising:
- (a) identifying a patient having breast cancer that is not known to have metastasized;
- (b) determining Breast Cancer Specific Gene (BCSG) polynucleotide levels in cells, tissues, or whole blood from said patient; and
- (c) comparing the determined BCSG polynucleotide levels with levels of BCSG polynucleotide in cells, tissue, or whole blood of a normal human control, wherein an increase in determined BCSG polynucleotide levels in the patient versus the normal human control is associated with breast cancer which has metastasized and wherein the BCSG polynucleotide comprises SEQ ID NO:18.

18. A method of staging breast cancer in a patient having breast cancer comprising:
- (a) identifying a patient having breast cancer;
- (b) determining Breast Cancer Specific Gene (BCSG) polynucleotide levels in a sample of cells, tissue, or whole blood from said patient; and
- (c) comparing determined BCSG polynucleotide levels with levels of BCSG polynucleotide in cells, tissues, or whole blood of a normal human control, wherein an increase in determined BCSG polynucleotide levels in said patient versus the normal human control is associated with breast cancer which is progressing and a decrease in the determined BCSG polynucleotide levels is associated with breast cancer which is regressing or in remission and wherein the BCSG polynucleotide comprises SEQ ID NO:18.

19. A method of monitoring breast cancer in a patient for the onset of metastasis comprising:
- (a) identifying a patient having breast cancer that is not known to have metastasized;
- (b) periodically determining levels of Breast Cancer Specific Gene (BCSG) polynucleotide in samples of cells, tissues, or whole blood from said patient; and
- (c) comparing the periodically determined BCSG polynucleotide levels with levels of BCSG polynucleotide in cells, tissues, or whole blood of a normal human control, wherein an increase in any one of the periodically determined BCSG polynucleotide levels in the patient versus the normal human control is associated with breast cancer which has metastasized and wherein the BCSG polynucleotide comprises SEQ ID NO:18.

20. A method of monitoring a change in stage of breast cancer in a patient comprising:
- (a) identifying a patient having breast cancer;
- (b) periodically determining levels of Breast Cancer Specific Genes (BCSG) polynucleotide in cells, tissues, or whole blood from said patient; and
- (c) comparing the periodically determined BCSG polynucleotide levels with levels of BCSG polynucleotide in cells, tissues, or whole blood of a normal human control, wherein an increase in any one of the periodically determined BCSG polynucleotide levels in the patient versus the normal human control is associated with breast cancer which is progressing in stage and a decrease in associated with breast cancer which is regressing in stage or in remission and wherein the BCSG polynucleotide comprises SEQ ID NO:18.

21. The method of claim 1 wherein levels of BCSG polynucleotide are determined in cells.

22. The method of claim 1 wherein levels of BCSG polynucleotide are determined in tissues.

23. The method of claim 1 wherein levels of BCSG polynucleotide are determined in whole blood.

24. The method of claim 2 wherein levels of BCSG polynucleotide are determined in cells.

25. The method of claim 2 wherein levels of BCSG polynucleotide are determined in tissues.

26. The method of claim 2 wherein levels of BCSG polynucleotide are determined in whole blood.

27. The method of claim 3 wherein levels of BCSG polynucleotide are determined in cells.

28. The method of claim 3 wherein levels of BCSG polynucleotide are determined in tissues.

29. The method of claim 3 wherein levels of BCSG polynucleotide are determined in whole blood.

30. The method of claim 4 wherein levels of BCSG polynucleotide are determined in cells.

31. The method of claim 4 wherein levels of BCSG polynucleotide are determined in tissues.

32. The method of claim 4 wherein levels of BCSG polynucleotide are determined in whole blood.

33. The method of claim 5 wherein levels of BCSG polynucleotide are determined in cells.

34. The method of claim 5 wherein levels of BCSG polynucleotide are determined in tissues.

35. The method of claim 5 wherein levels of BCSG polynucleotide are determined in whole blood.

36. The method of claim 16 wherein levels of BCSG polynucleotide are determined in cells.

37. The method of claim 16 wherein levels of BCSG polynucleotide are determined in tissues.

38. The method of claim 16 wherein levels of BCSG polynucleotide are determined in whole blood.

39. The method of claim 17 wherein levels of BCSG polynucleotide are determined in cells.

40. The method of claim 17 wherein levels of BCSG polynucleotide are determined in tissues.

41. The method of claim 17 wherein levels of BCSG polynucleotide are determined in whole blood.

42. The method of claim 18 wherein levels of BCSG polynucleotide are determined in cells.

43. The method of claim 18 wherein levels of BCSG polynucleotide are determined in tissues.

44. The method of claim 18 wherein levels of BCSG polynucleotide are determined in whole blood.

45. The method of claim 19 wherein levels of BCSG polynucleotide are determined in cells.

46. The method of claim 19 wherein levels of BCSG polynucleotide are determined in tissues.

47. The method of claim 19 wherein levels of BCSG polynucleotide are determined in whole blood.

48. The method of claim 20 wherein levels of BCSG polynucleotide are determined in cells.

49. The method of claim 20 wherein levels of BCSG polynucleotide are determined in tissues.

50. The method of claim 20 wherein levels of BCSG polynucleotide are determined in whole blood.

* * * * *

SEQUENCE LISTING

<160> NUMBER OF SEQ ID NOS: 21

<210> SEQ ID NO 1
<211> LENGTH: 1078
<212> TYPE: DNA
<213> ORGANISM: Homo sapiens

<400> SEQUENCE: 1

```
ggatgataca agagccaaga agggacattt gagttgtgtc gcttagatag gaaagggatc      60
cagggaaaat caacagtaag tgaggatgag cagcgtctct tggttttcat tgaggataga     120
gtaagagatt gagtttagat tgcaacagaa ggaattagtt tagataccag gaagaacttc     180
ctagcctgaa gatttgtcat agtgtctgct ttctagatat ctgggaaaga tttgataata     240
gttgtttgtg aatagaaagg aggatatgat gtttttattg gccattttgc gggactcttc     300
gacttcttgc tgctgtctct tgaggataca ttccaattcc atcctggcga gatccaagtg     360
cttacgtact gtctccttag ctgccttaga gtaaacgatc atcagttcaa tggaccaaaa     420
tcaccttcag ccatgtggtt tcttcatcat catggatttc ttttggttga caaacattct     480
ggctctcaga tgcaaaaagt cacactggga aatgaactgt aagtggtgaa attagttttg     540
gtatttaatt taaaactaca ttttagtttt tctcttctct tctatgttgc aatgaatgta     600
aagtatttgg gatccagtgc ttataaacct ttccttcctt tgtgcacaga atgtaactag     660
caagcccatt agcacccaga taattctatc atgttagttt cccatcctgg aaaatctttg     720
tacagtggga agttccccga tgtgttttc tttcttaggt gaagggttgg ctatatcact     780
ttattgaatt ttgcattcct tagactttta aaatatacta atgtattcta gtcttactct     840
aaagaccttt gatgttaaag gaatccttca tttatttcat attccctatc tcatagggcc     900
acaattattt taatacagag atgattttca aaatatttta acaactggta caggacagat     960
gccagccact cagaagggat gcctgctgta aacaagcagt atgtatggtt gtaccaatgc    1020
ctattggctg aacattatgc tactttcaga tattaaaatg gtgttccttt gaatcgtg     1078
```

<210> SEQ ID NO 2
<211> LENGTH: 1713
<212> TYPE: DNA
<213> ORGANISM: Homo sapiens

<400> SEQUENCE: 2

```
atcgcattgc accaggatga ctctgaaatg gacttcagtt cttctgctga tacatctcca      60
gttgttactt tagctctggg agttgtggaa aagtgctggt gtgggccgca gaatacagcc     120
attggatgaa tatgaagaca atcctgaaag agcttgttca gagaggtcat gaggtgactg     180
tactggcatc ttcagcttcc attcttttg atcccaatga tgcatccact cttaaatttg     240
aagtttatcc tacatcttta actaaaactg aatttgagaa tatcatcatg caacaggtta     300
agagatggtc agacattcga aaagatagct tttggttata ttttcacaa gaacaagaaa     360
tcctgtggga attatatgac atatttagaa acttctgtaa agatgtagtt tcaaataaga     420
aagttatgaa aaaactacaa gagtcaagat ttgacatcgt ttttgcagat gctgttttc      480
```

-continued

```
cctgtggtga gctgctggct gcgctactta acatacggtt tgtgtacagt ctccgctta      540 ctcctggcta cacaattgaa aggcacagtg gaggactgat tttccctcct tcctacatac     600
ctattgttat gtcaaaatta agtgatcaaa tgactttcat ggagagggta aaaatatga      660 tctatgtgct ttattttgac ttttggttcc aaatgtctga tatgaagaag tgggatcagt     720
tttacagtga agtttaggga agacccacta ccttatttga dacaatggga aaagctgaca     780
tatggcttat gcgaaactcc tggagttttc aatttcctca tccattctta ccaaacgttg     840
attttgttgg aggattccac tggcaaacct gccaaacccc tacctaagga aatggaggag     900
tttgtacaga gctctggaga aaatggtgtt gtggtgtttt ctctggggtc agtgataagt     960
aacatgacag cagaaagggc caatgtaatt gcaacagccc ttgccaagat cccacaaaag    1020
gttctgtgga gatttgatgg gaataaacca gatgccttag gtctcaatac tcggctgtat    1080
aagtggatac cccagaatga ccttctaggt catccaaaaa ccagagcttt tataactcat    1140
ggtggagcca atggcatcta tgaggcaatc taccatggga tccctatggt gggcattcca    1200
ttgttttggg atcaacctga taacattgct cacatgaagg ccaagggagc agctgttaga    1260
ttggacttca acacaatgtc gagtacagac ctgctgaatg cactgaagac agtaattaat    1320
gatcctttat ataaagagaa tattatgaaa ttatcaagaa ttcaacatga tcaaccagta    1380
aagcccctgg atcgagcagt cttctggatt gaatttgtca tgccccacaa aggagccaaa    1440
caccttcgag ttgcagccca tgacctcacc tggttccagt accactcttt ggatgtgatt    1500
gggtttctgc tggcctgtgt ggcaactgtg atatttatca tcacaaagtt ttgtctgttt    1560
tgtttctgga agtttgctag aaaagggaag aagggaaaaa gagattagtt atgtctgaca    1620
tttgaagctg gaaaaccaga tagataggac aacttcagtt tattccagca agaaagaaaa    1680
gattgttatg caagatttct ttcttcctgt gac                                 1713
```

<210> SEQ ID NO 3
<211> LENGTH: 2327
<212> TYPE: DNA
<213> ORGANISM: Homo sapiens
<220> FEATURE:
<221> NAME/KEY: unsure
<222> LOCATION: (924)
<221> NAME/KEY: unsure
<222> LOCATION: (1678)..(1704)

<400> SEQUENCE: 3

```
gatggatgca tctcaaaatg tatagccaga cttgagaggt gacaattaaa gatctaaaaa      60
agagaggaga ttcccccaaa caacaatatt taattttctt agtaaaaaga ataacagaat     120
gcatcgtggc aatccttaag caacattatc tatgtggact gcttaaatca gcaaaacacc     180
agaagtttgg ttaacttggg caatatgaca agtattactt tttgggcaaa actactcatt     240
aagcaatttc tctagtgtgt cggacacaaa taggttcttt attttttgca tgtatgcctt     300
tttattttca ttcaattttt ttttttctc agacagacat agtagtaacg actagcattg     360
gaaaatacat atcactattc ttggaatatt tatggtcagt ctacttttta gtagaatatt     420
tttggatagc gttgacacga tagatcttat tccatacttc tttattattg ataatttat     480 tttcattttt tgctttcatt attatacata ttttggtgga gaagaggttg ggctttttg     540 aaagagacaa aaatttatta taacactaaa cactcctttt tgacatatt aaagccttta     600 ttccatctct caagatatat tataaaattt attttttaa tttagatttt ctgaattatt     660
ttatcttaaa ttgtgatttt aaacgagcta ttatggtacg gaactttttt taatgaggaa    720
```

```
tttcatgatg atttaggaat tttctctctt ggaaaaggct tcccctgtga tgaaaatgat      780
gtgccagcta aaattgtgtg ccatttaaaa actgaaaata ttttaaaatt atttgtctat      840
attctaaatt gagctttgga tcaaacttta ggccaggacc agctcatgcg ttctcattct      900
tccttttctc actctttctc tcancactca cctctgtatt cattctgttg tttgggatag      960
aaaaatcata aagagccaac ccatctcaga acgttgtgga ttgagagaga cactacatga     1020
ctccaagtat atgagaaaag gacagagctc taattgataa ctctgtagtt caaaggaaa      1080 agagtatgcc caattctctc tacatgacat attgagattt tttttaatca acttttaaga     1140
tagtgatgtt ctgttctaaa ctgttctgtt ttagtgaagg tagatttta taaaacaagc      1200 atggggattc ttttctaagg taatattaat gagaagggaa aaagtatct ttaacagctc      1260 tttgttgaag cctgtggtag cacattatgt ttataattgc acatgtgcac ataatctatt     1320
atgatccaat gcaaatacag ctccaaaaat attaaatgta tatatatttt aaaatgcctg     1380
aggaaataca tttttcttaa taaactgaag agtctcagta tggctattaa ataattatt     1440 agcctcctgt tgtgtggctg caaaacatca caaagtgacc ggtcttgaga cctgtgaact     1500
gctgccctgt ttagtaaata aaattaatgc atttctagag ggggaatatc tgccatccag     1560
tggtggaaat gtggagtaaa gaagctggtg gtctgcttct gtgctgtatg ccagcctttt    1620
gccttaagtt gagaggaggt caactttagc tactgtcttt ggtttgagag ccatggcnnn    1680 nnnnnnnnn nnnnnnnnnn nnngtcgtc tttggtgagc cagtaaggtg aaagcttgct    1740
gactgtccaa ggcacaagag aaaattgagg aattgaaatg caacctgagt atcaaactaa    1800
atattctaat caaggtagg tactgttagg tggaattcta tcagcaggca actgcaaatg     1860
agaagaagat agaaggacgc ccgtcgggac tttggagggc agtgttattt tcccaaagaa    1920
agacggccaa gggcagaggc atggattctt tgcagagcac ttccttttgg ttttcagta    1980 ctgtttcata gacagtgggc tcacatgttc ctgatagtgc tgcagttgct tagaaagcat    2040
cccagttatt gcagtaatta gaacttctgg aatatgctag ggcagaagta tgtcaagtat    2100
gtcacatgaa gaaatgtga aattcaagag taatccacac gtgagaaact agacaatgta    2160
cattcatgtg ttctcttgaa aggaaaggga gagctgtaag cttcactctg tcctacaccg    2220
gagaaaagca ggaataactt taccgtggaa ataatgttta gcttttatgc agagaaaatt    2280
gtccttccta gagcatagag tcccaaaact caattctggt tttcccc                   2327
```

<210> SEQ ID NO 4
<211> LENGTH: 639
<212> TYPE: DNA
<213> ORGANISM: Homo sapiens

<400> SEQUENCE: 4

```
ccagaaccga gtttaggtcc aggttctcgt tctggcaaat cttctcctt accttcttcc       60
```

```
tccacccctc cacctatgcc atgttttccc ttagccactc cccagctcgg tggaggaaag      120
gcaggcctaa ctaggtaccg tcttcccgac tttgctcaat gatagctggg tgggtctagc      180
tgggttccag ccacttgtaa tgtgggacat ctctcacccc aactttgtag gtggagcaac      240
tgctacagag gtaaatatga ttaactttac attccatctt tcgtctgctc ccaaacttaa      300
cagcaggtaa tctgcttcta gcaagtggtg aaggtaagag aagcatctgt ataggaggca      360
agagatctga gtccttttga aggcctatcc tctgctctgt atctcaatta ctgttcttca      420
tttcaattat tcttacctac tattcagttc ccttgatctt tcttcttggg ggctgtctt      480 agggtcaggg agattgcaga agcaccagaa ctaggagcag ccctgagaca tggggagttg      540
gagctgaagg aggaatggca ggatgaagaa ttccctaggt gaggacgtgt gagggtggct      600
gggagaaggg agggtggtc acgaatggac ggaggggat                              639

<210> SEQ ID NO 5
<211> LENGTH: 779
<212> TYPE: DNA
<213> ORGANISM: Homo sapiens

<400> SEQUENCE: 5
gtatacattc tttattaatc attttgcttc caacccccatt tagcctgcca ttgaaatgca      60
aaagtctgtt ccaataaag ccttggaatt gaagaatgaa caaacattga gagcagatga      120
gatactccca tcagaatcca aacaaaagga ctatgaagaa agttcttggg attctgagag      180
tctctgtgag actgtttcac agaaggatgt gtgtttaccc aaggctacac atcaaaaaga      240
aatagataaa ataaatggaa aattagaagg gtctcctgtt aaagatggtc ttctgaaggc      300
taactgcgga atgaaagttt ctattccaac taaagcctta gaattgatgg acatgcaaac      360
tttcaaagca gagcctcccg agaagccatc tgccttcgag cctgccattg aaatgcaaaa      420
gtctgttcca ataaagcct tggaattgaa gaatgaacaa acattgagag cagatcagat      480
gttcccttca gaatcaaaac aaaagaaggt tgaagaaaat tcttgggatt ctgagagtct      540
ccgtgagact gtttcacaga aggatgtgtg tgtacccaag gctacacatc aaaagaaat      600 ggataaaata agtggaaaat tagaagattc aactagccta tcaaaaatct tggatacagt      660
tcattcttgt gaaagagcaa gggaacttca aaaagatcac tgtgaacaac gtacaggaaa      720
aatggaacaa atgaaaaaga agtttttgtgt actgaaaaag aaactgtcag aagcaaaaa      779

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 6
accccattta gcctgccat                                                    19

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 7
atgggagtat ctcatctgct ctca                                              24
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 8
tgtttgttca ttcttcaatt ccaaggcttt                               30

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 9
gcccattagc acccagataa t                                        21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 10 gccaacccctt cacctaagaa a                                       21

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 11
cttcccactg tacaaagatt ttccaggatg                               30

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 12
cctggagttt tcaatttcct ca                                       22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 13
ccccagagaa aacaccacaa                                          20

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 14
actcctccat ttccttaggt aggggtttg                                                29

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 15
gagcacttcc ttttggtttt tc                                                       22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 16
gccctagcat attccagaag ttc                                                      23

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic

<400> SEQUENCE: 17
tagacagtgg gctcacatgt tcctgatagt g                                             31

<210> SEQ ID NO 18
<211> LENGTH: 1722
<212> TYPE: DNA
<213> ORGANISM: Homo sapiens

<400> SEQUENCE: 18
tgcaccagga tgactctgaa atggacttca gttcttctgc tgatacatct cagttgttac      60
tttagctctg ggagttgtgg aaaagtgctg gtgtgggccg cagaatacag ccattggatg     120
aatatgaaga caatcctgaa agagcttgtt cagagaggtc atgaggtgac tgtactggca     180
tcttcagctt ccattctttt tgatcccaat gatgcatcca ctcttaaatt tgaagtttat     240
cctacatctt taactaaaac tgaatttgag aatatcatca tgcaacaggt taagagatgg     300
tcagacattc gaaaagatag cttttggtta tattttcac aagaacaaga atcctgtgg      360
gaattatatg acatatttag aaacttctgt aaagatgtag tttcaaataa gaaagttatg     420
aaaaaactac aagagtcaag atttgacatc gtttttgcag atgctgtttt tcccgtggt      480
gagctgctgg ctgcgctact aacatacgg tttgtgtaca gtctccgctt tactcctggc      540
tacacaattg aaaggcacag tggaggactg attttccctc cttcctacat acctattgtt     600
atgtcaaaat taagtgatca aatgactttc atggagaggg taaaaatat gatctatgtg     660
ctttattttg acttttggtt ccaaatgtct gatatgaaga agtgggatca gttttacagt     720
gaagttttag gaagacccac taccttattt gagacaatgg gaaaagctga catatggctt     780
atgcgaaact cctggagttt tcaatttcct catccattct taccaaacgt tgatttgtt      840
ggaggattcc actgcaaacc tgccaaaccc ctacctaagg aaatggagga gtttgtacag    900

```
agctctggag aaaatggtgt tgtggtgttt tctctggggt cagtgataag taacatgaca    960
gcagaaaggg ccaatgtaat tgcaacagcc cttgccaaga tcccacaaaa ggttctgtgg   1020
agatttgacg ggaataaacc agatgcctta ggtctcaata ctcggctgta caagtggata   1080
ccccagaatg accttctagg tcatccaaaa accagagctt ttataactca tggtggagcc   1140
aatggcatct atgaggcaat ctaccatggg atccctatgg tgggcattcc attgtttttt   1200
gatcaacctg ataacattgc tcacatgaag gccaagggag cagctgttag attggacttc   1260
aacacaatgt cgagtacaga cctgctgaat gcactgaaga cagtaattaa tgatccttta   1320
tataaagaga atattatgaa attatcaaga attcaacatg atcaaccagt aaagcccctg   1380
gatcgagcag tcttctggat tgaatttgtc atgccccaca aaggagccaa acaccttcga   1440
gttgcagccc atgacctcac ctggttccag taccactctt tggatgtgat tgggtttctg   1500
ctggcctgtg tggcaactgt gatatttatc atcacaaagt tttgtctgtt ttgtttctgg   1560
aagtttgcta gaaagggaa gaagggaaaa agagattagt tatgtctgac atttgaagct   1620
ggaaaaccag atagatagga caacttcagt ttattccagc aagaaagaaa agattgttat   1680
gcaagatttc tttcttcctg tgacaaaaaa aaaaaaaaaa aa                     1722
```

<210> SEQ ID NO 19
<211> LENGTH: 529
<212> TYPE: PRT
<213> ORGANISM: Homo sapiens

<400> SEQUENCE: 19

```
Met Thr Leu Lys Trp Thr Ser Val Leu Leu Ile His Leu Ser Cys
 1               5                  10                  15

Tyr Phe Ser Ser Gly Ser Cys Gly Lys Val Leu Val Trp Ala Ala Glu
             20                  25                  30

Tyr Ser His Trp Met Asn Met Lys Thr Ile Leu Lys Glu Leu Val Gln
         35                  40                  45

Arg Gly His Glu Val Thr Val Leu Ala Ser Ser Ala Ser Ile Leu Phe
     50                  55                  60

Asp Pro Asn Asp Ala Ser Thr Leu Lys Phe Glu Val Tyr Pro Thr Ser
 65                  70                  75                  80

Leu Thr Lys Thr Glu Phe Glu Asn Ile Ile Met Gln Gln Val Lys Arg
                 85                  90                  95

Trp Ser Asp Ile Arg Lys Asp Ser Phe Trp Leu Tyr Phe Ser Gln Glu
                100                 105                 110

Gln Glu Ile Leu Trp Glu Leu Tyr Asp Ile Phe Arg Asn Phe Cys Lys
            115                 120                 125

Asp Val Val Ser Asn Lys Lys Val Met Lys Lys Leu Gln Glu Ser Arg
        130                 135                 140

Phe Asp Ile Val Phe Ala Asp Ala Val Phe Pro Cys Gly Glu Leu Leu
145                 150                 155                 160

Ala Ala Leu Leu Asn Ile Arg Phe Val Tyr Ser Leu Arg Phe Thr Pro
                165                 170                 175

Gly Tyr Thr Ile Glu Arg His Ser Gly Gly Leu Ile Phe Pro Pro Ser
            180                 185                 190

Tyr Ile Pro Ile Val Met Ser Lys Leu Ser Asp Gln Met Thr Phe Met
        195                 200                 205

Glu Arg Val Lys Asn Met Ile Tyr Val Leu Tyr Phe Asp Phe Trp Phe
    210                 215                 220

Gln Met Ser Asp Met Lys Lys Trp Asp Gln Phe Tyr Ser Glu Val Leu
```

```
                    225                 230                 235                 240
Gly Arg Pro Thr Thr Leu Phe Glu Thr Met Gly Lys Ala Asp Ile Trp
                245                 250                 255
Leu Met Arg Asn Ser Trp Ser Phe Gln Phe Pro His Pro Phe Leu Pro
            260                 265                 270
Asn Val Asp Phe Val Gly Gly Phe His Cys Lys Pro Ala Lys Pro Leu
        275                 280                 285
Pro Lys Glu Met Glu Glu Phe Val Gln Ser Ser Gly Glu Asn Gly Val
    290                 295                 300
Val Val Phe Ser Leu Gly Ser Val Ile Ser Asn Met Thr Ala Glu Arg
305                 310                 315                 320
Ala Asn Val Ile Ala Thr Ala Leu Ala Lys Ile Pro Gln Lys Val Leu
                325                 330                 335
Trp Arg Phe Asp Gly Asn Lys Pro Asp Ala Leu Gly Leu Asn Thr Arg
            340                 345                 350
Leu Tyr Lys Trp Ile Pro Gln Asn Asp Leu Leu Gly His Pro Lys Thr
        355                 360                 365
Arg Ala Phe Ile Thr His Gly Gly Ala Asn Gly Ile Tyr Glu Ala Ile
    370                 375                 380
Tyr His Gly Ile Pro Met Val Gly Ile Pro Leu Phe Phe Asp Gln Pro
385                 390                 395                 400
Asp Asn Ile Ala His Met Lys Ala Lys Gly Ala Ala Val Arg Leu Asp
                405                 410                 415
Phe Asn Thr Met Ser Ser Thr Asp Leu Leu Asn Ala Leu Lys Thr Val
            420                 425                 430
Ile Asn Asp Pro Leu Tyr Lys Glu Asn Ile Met Lys Leu Ser Arg Ile
        435                 440                 445
Gln His Asp Gln Pro Val Lys Pro Leu Asp Arg Ala Val Phe Trp Ile
    450                 455                 460
Glu Phe Val Met Pro His Lys Gly Ala Lys His Leu Arg Val Ala Ala
465                 470                 475                 480
His Asp Leu Thr Trp Phe Gln Tyr His Ser Leu Asp Val Ile Gly Phe
                485                 490                 495
Leu Leu Ala Cys Val Ala Thr Val Ile Phe Ile Ile Thr Lys Phe Cys
            500                 505                 510
Leu Phe Cys Phe Trp Lys Phe Ala Arg Lys Gly Lys Lys Gly Lys Arg
        515                 520                 525
Asp

<210> SEQ ID NO 20
<211> LENGTH: 10006
<212> TYPE: DNA
<213> ORGANISM: Homo sapiens

<400> SEQUENCE: 20
ttcctccgcg aaggctcctt tgatattaat agtgttggtg tcttgaaact gacgtaatgc      60
gcggagactg aggtcctgac aagcgataac atttctgata agacccgat cttactgcaa     120
tctctagcgt cctcttttt ggtgctgctg gtttctccag acctcgcgtc ctctcgattg     180
ctctctcgcc ttcctatttc tttttttttt ttaaacaa aaaacaacac cccctcccct     240
ctcccacccg gcaccgggca catccttgct ctatttcctt tctctttctc tctctctc     300
tctctttttt aataagggtg ggggagggaa agggggggga ggcaggaaag acctttttct     360
ctcccccccg caataatcca agatcaactc tgcaaacaac agaagacggt tcatggcttt     420
```

-continued

```
ggccgccgcg ccaccatctt tcgggctgcc gagggtgttc ttgacgatta atcaacagat      480
gtacagatca gctctcaaaa tgtcttctgt gtcttctgag cgtcttctaa gacaattgca      540
ttagcctcct gctagttgac taatagaatt aataattgta aaaagcactc taaagccaca      600
tgccttatga agtcaatgct gggtatgatt ttacaaatat ggtccggaaa agaaccccc       660 ctctgagaaa cgttgcaagt gaaggcgagg gccagatcct ggagcctata ggtacagaaa      720
gcaaggtatc tggaaagaac aaagaattct ctgcagatca gatgtcagaa atacggatc       780 agagtgatgc tgcagaacta atcataagg aggaacatag cttgcatgtt caagatccat       840
cttctagcag taagaaggac ttgaaaagcg cagttctgag tgagaaggct ggcttcaatt      900
atgaaagccc cagtaaggga ggaaactttc cctcctttcc gcatgatgag gtgacagaca      960
gaaatatgtt ggctttctca tttccagctg ctgggggagt ctgtgagccc ttgaagtctc     1020
cgcaaagagc agaggcagat gaccctcaag atatggcctg caccccctca ggggactcac     1080
tggagacaaa ggaagatcag aagatgtcac caaaggctac agaggaaaca gggcaagcac     1140
agagtggtca agccaattgt caaggtttga gcccagtttc agtggcctca aaaaacccac     1200
aagtgccttc agatgggggt gtaagactga ataaatccaa aactgactta ctggtgaatg     1260
acaacccaga cccggcacct ctgtctccag agcttcagga cttaaatgc aatatctgtg      1320 gatatggtta ctacggcaac gaccccacag atctgattaa gcacttccga aagtatcact     1380
taggactgca taaccgcacc aggcaagatg ctgagctgga cagcaaaatc ttggcccttc     1440
ataacatggt gcagttcagc cattccaaag acttccagaa ggtcaaccgt tctgtgtttt     1500
ctggtgtgct gcaggacatc aattcttcaa ggcctgtttt actaaatggg acctatgatg     1560
tgcaggtgac ttcaggtgga acattcattg gcattggacg gaaaacacca gattgccaag     1620
ggaacaccaa gtatttccgc tgtaaattct gcaatttcac ttatatgggc aactcatcca     1680
ccgaattaga caacattttt cttcagactc acccaaacaa aataaaagct tctctcccct     1740
cctctgaggt tgcaaaacct tcagagaaaa actctaacaa gtccatccct gcacttcaat     1800
ccagtgattc tggagacttg ggaaaatggc aggacaagat aacagtcaaa gcaggagatg     1860
acactcctgt tgggtactca gtgcccataa agcccctcga ttcctctaga caaaaggtac     1920
agaggccacc agttactact ggtgtaaatt ttgtagtttc agctgtgagt catctagctc     1980
acttaaactg ctagaacatt atggcaagca gcacggagca gtgcagtcag gcggccttaa     2040
tccagagtta aatgataagc tttccagggg ctctgtcatt aatcagaatg atctagccaa     2100
aagttcagaa ggagagacaa tgaccaagac agacaagagc tcgagtgggg ctaaaaagaa     2160
ggacttctcc agcaagggag ccgaggataa tatggtaacg agctataatt gtcagttctg     2220
tgacttccga tattccaaaa gccatggccc tgatgtaatt gtagtggggc acttctccg      2280 tcattatcaa cagctcccata acattcacaa gtgtaccatt aaacactgtc cattctgtcc     2340
cagaggactt tgcagcccag aaaagcacct tggagaaatt acttatccgt ttgcttgtag     2400
aaaaagtaat tgttcccact gtgcactctt gcttctgcac ttgtctcctg gggcggctgg     2460
aagctcgcga gtcaaacatc agtgccatca gtgttcattc accacccctg acgtagatgt     2520
actcctcttt cactatgaaa gtgtgcatga gtcccaagca tcggatgtca acaagaagc      2580 aaatcacctg caaggatcgg atgggcagca gtctgtcaag gaaagcaaag aacactcatg     2640
taccaaatgt gatttttatta cccaagtgga agaagagatt tccgacact acaggagagc      2700 acacagctgc tacaaatgcc gtcagtgcag ttttacagct gccgatactc agtcactact     2760
```

```
ggagcacttc aacactgttc actgccagga acaggacatc actacagcca acggcgaaga    2820
ggacggtcat gccatatcca ccatcaaaga ggagcccaaa attgacttca gggtctacaa    2880
tctgctaact ccagactcta aaatgggaga gccagtttct gagagtgtgg tgaagagaga    2940
gaagctggaa gagaaggacg ggctcaaaga gaaagtttgg accgagagtt ccagtgatga    3000
ccttcgcaat gtgacttgga gaggggcaga catcctgcgg gggagtccgt catacaccca    3060
agcaagcctg gggctgctga cgcctgtgtc tggcacccaa gagcagacaa agactctaag    3120
ggatagtccc aatgtggagg ccgcccatct ggcgcgacct atttatggct ggctgtgga    3180 aaccaaggga ttcctgcagg gggcgccagc tggcggagaa gtctggggg ccctccccca    3240 gcagtatcct gcatcgggag aaaacaagtc aaggatgaa tcccagtccc tgttacggag    3300
gcgtagaggc tccggtgttt tttgtgccaa ttgcctgacc acaaagacct ctctctggcg    3360
aaagaatgca aatggcggat atgtatgcaa cgcgtgtggc ctctaccaga agcttcactc    3420
gactcccagg cctttaaaca tcattaaaca aaacaacggt gagcagatta ttaggaggag    3480
aacaagaaag cgccttaacc cagaggcact tcaggctgag cagctcaaca acagcagag    3540 gggcagcaat gaggagcaag tcaatggaag cccgttagag aggaggtcag aagatcatct    3600
aactgaaagt caccagagag aaattccact ccccagccta agtaaatacg aagcccaggg    3660
ttcattgact aaaagccatt ctgctcagca gccagtcctg gtcagccaaa ctctggatat    3720
tcacaaaagg atgcaaccct tgcacattca gataaaaagt cctcaggaaa gtactggaga    3780
tccaggaaat agttcatccg tatctgaagg gaaaggaagt tctgagagag gcagtccat    3840 agaaaagtac atgagacctg cgaaacaccc aaattattca ccaccaggca gccctattga    3900
aaagtaccag tacccacttt ttggacttcc cttttacata atgacttcca gagtgaagct    3960
gattggctgc ggttctggag taaatataag ctctccgttc ctgggaatcc gcactacttg    4020
agtcacgtgc ctggcctacc aaatccttgc caaaactatg tgccttatcc caccttcaat    4080
ctgcctcctc attttcagc tgttggatca gacaatgaca ttcctctaga tttggcgatc    4140
aagcattcca gacctgggcc aactgcaaac ggtgcctcca aggagaaaac gaaggcacca    4200
ccaaatgtaa aaaatgaagg tcccttgaat gtagtaaaaa cagagaaagt tgatagaagt    4260
actcaagatg aactttcaac aaaatgtgtg cactgtggca ttgtctttct ggatgaagtg    4320
atgtatgctt tgcatatgag ttgccatggt gacagtggac ctttccagtg cagcatatgc    4380
cagcatcttt gcacggacaa atatgacttc acaacacata tccagagggg cctgcatagg    4440
aacaatgcac aagtggaaaa aaatggaaaa cctaaagagt aaaaccttag cacttagcac    4500
aattaaatag aaataggttt tcttgatggg aattcaatag cttgtaatgt cttatgaaga    4560
cctattaaaa aaatacttca tagagcctgc cttatccaac atgaaattcc cttcttttgt    4620
tattctttct tttgatgagt aggttaccaa gattaaaaag tgagataaat ggtcaatgag    4680
aaagaatgga agatggtaaa caatcacttt ttaaaacctg ttaagtcaaa accatcttgg    4740
ctaatatgta ctgggaaat aatccataag agatatcacc agactagaat taatatattt    4800 ataagaaag agaccaaaac tgtctagaat ttgaagggt ttacatatta ttatactaaa    4860
gcagtactgg actggccatt ggaccatttg ttccaaaacc cataaattgt tgcctaaatt    4920
tataatgatc atgaaaccct aggcagagga ggagaaattg aaggtccagg gcaatgaaag    4980
aaaaatggcg ccctctcaat ttagtcttct ctcattggcc atgtttcaga ttttgaccta    5040
gaaatgcgag ctgtggttag gcttggttag agtgcagcaa gcaacatgac agatggtggc    5100
acgctgtttt tacccagccc tgcctgtaca tacacatgca caccctctct gatattttg    5160
```

```
tcctttagat gttcaaatac tcagtagtcc ttttgtttgc ggtttagatt cattttgtcc   5220
acacatgtac ccattttaaa aaacaatgtc ctcgatgctt ctgtagtgat ttcattttag   5280
ccaggtattt ctttcttgtg tgtgatgaac cagtatggat ttgcttttct aagcctcctg   5340
ttggttacta atctcacttg gcacattata actaaaggaa tccccctcaat tcaaaagcat   5400 agatggatac aaatgtcaga ccgtgggttt aatttgttta gaacacatgg catttcttca   5460
caaggtaacc tgctgtattt atttattttc ttttggttaa ataataattc caaactttgt   5520
ggtcaggcag cgtctaaggt tacgttacca cagactgaca gttggtatat gtaccagcca   5580
atcccttcat taaatgtata cagatttagt taagtagcat taaataggat tcttagaagt   5640
atgtcctcat agaacttta atacttaagg ctttgtaaaa actatccatg aagggaaagc   5700
tcctcagcat aactgctcag ggaaataggg ctaaataact gaacattaaa taattggtta   5760
aaggtgctgt tagtcgagcc tcaatgcttg ctacaaggat gtatgtacaa ggactgactt   5820
taataatttg cattatattg tcccaaccag tagtttattt tttgccacgg agatgtagaa   5880
gatattacaa gctactggat gcactgtcag attaacttat ttcattaaag aagttgggag   5940
aacaaatagg aaaaaaaaac ttatttttct agtaaatatt aatgtattac atttcaaata   6000
atggtgcctg acatattgaa taattatttt ctacagtgta cgtatgcaac aaagatattc   6060
catcatgcat tagagtcagt tctggctctg cctagctgtt tacatttgca aatgtagcaa   6120
acaaggtaat gaagcaacta tttctattgc agtagatatc cttttgtgtg tgtgtgtgtg   6180
cattaaagtt gtaaacggta acatgaaaca aatgaaagtt cttgctataa tggtatggaa   6240
aacaagaagg aaatgaaaat attttttatgc ctacttagga aaaaaagggt agcacttatt   6300
cattccaagt acttttttt ttttaatttt taagctctta actcacattg ttatgcttaa   6360
gatgataaac atatatcctc tttttattgc tttgtctatg tttcatatga aacatttcag   6420
aaattatttt gataagtgtt gctggaatct gcaacgctga tttttttttg cattctgtag   6480
tcgcatttgc actccatttt tacattaatt cgcagttgct ttgtatcatt gttttgtttg   6540
ggttttgttt ctttttcaca gtgccgggtc ttcgtttctt aaagttggat ggcaggtaga   6600
gttcaaccag ttcgtgactg ttgtagcgaa tgaagttaaa aaaatgtctt tctgatgttg   6660
tgttgtcatt tcattttgg catttttttg tttgcatatt aaaaaaagag aaaagagaaa   6720
gcaagagaca gaaatcagga ctaagtcctc tgcttcagtt tcattgttaa cgggccttat   6780
tctgatctca cctgtcgcgt agctctaata ttcacataaa ctgaaataaa gaagtggaat   6840
gaggagcttt gacattcaaa ttatgtgatg taatttatct tccttaggaa ttttgatgga   6900
tgcatctcaa aatgtatagc cagacttgag aggtgacaat taaagatcta aaaagagag   6960 gagattcccc caaacaacaa tatttaattt tcttagtaaa aagaataaca gaatgcatcg   7020 tgcaatcct taagcaacat tatctatgtg gactgcttaa atcagcaaaa caccagaagt   7080
ttggttaact tgggcaatat gacaagtatt acttttggg caaaactact cattaagcaa   7140
tttctctagt gtgtcggaca caaataggtt ctttattttt ggcatgtatg ccttttatt   7200 ttcattcaat tttttttttt tctcagacag acatagtagt atcaactagc attggaaaat   7260
acatatcact attcttggaa tatttatggt cagtctactt tttagtaaaa atttttggga   7320
tagcgttgac acgatagatc ttattccata cttctttatt attgataatt ttattttcat   7380
tttttgcttt cattattata catatttgg tggagaagag gttgggcttt ttgaaagag   7440 acaaaaattt attataacac taaacactcc ttttttgaca tattaaagcc tttattccat   7500
```

-continued

```
ctctcaagat atattataaa atttattttt ttaatttaag atttctgaat tattttatct    7560
taaattgtga ttttaaacga gctattatgg tacggaactt tttttaatga ggaatttcat    7620
gatgatttag gaattttctc tcttggaaaa ggcttcccct gtgatgaaaa tgatgtgcca    7680
gctaaaattg tgtgccattt aaaaactgaa aatattttaa aattatttgt ctatattcta    7740
aattgagctt tggatcaaac tttaggccag gaccagctca tgcgttctca ttcttccttt    7800
tctcactctt tctctcatca ctcacctctg tattcattct gttgtttggg atagaaaaat    7860
cataaagagc caacccatct cagaacgttg tggattgaga gagacactac atgactccaa    7920
gtatatgaga aaaggacaga gctctaattg ataactctgt agttcaaaag gaaagagtat    7980
gcccaattct ctctacatga catattgaga ttttttttaa tcaactttta agatagtgat    8040
gttctgttct aaactgttct gttttagtga aggtagattt ttataaaaca agcatgggga    8100
ttcttttcta aggtaatatt aatgagaagg gaaaaaagta tctttaacag ctctttgttg    8160
aagcctgtgg tagcacatta tgtttataat tgcacatgtg cacataatct attatgatcc    8220
aatgcaaata cagctccaaa aatattaaat gtatatatat tttaaaatgc ctgaggaaat    8280
acatttttct taataaactg aagagtctca gtatggctat taaaataatt attagcctcc    8340
tgttgtgtgg ctgcaaaaca tcacaaagtg accggtcttg agacctgtga actgctgccc    8400
tgtttagtaa ataaaattaa tgcatttcta gaggggggaat atctgccatc cagtggtgga    8460
aatgtggagt aaagaagctg gtggtctgct tctgtgctgt atgccagcct tttgccttaa    8520
gttgagagga ggtcaacttt agctactgtc tttggttTga gagccatggc aaaaaaaaa    8580
aaagaaaaaa agatcaagtc gtctttggtg agccagtaag gtgaaagctt gctgactgtc    8640
caaggcacaa gagaaaattg aggaattgaa atgcaacctg agtatcaaac taaatattct    8700
aatcaaaggt aggtactgtt aggtggaatt ctatcagcag gcaactgcaa atgagaagaa    8760
gatagaagga cgcccgtcgg gactttggag ggcattgtta ttttcccaaa gaaagacggc    8820
caagggcaga ggcatggatt ctttgcagag cacttccttt tggttttTca gtactgtttc    8880
atagacagtg ggctcacatg ttcctgatag tgctgcagtt gcttagaaag catcccagtt    8940
aattgcagta attagaactt ctggaatatg ctagggcaga agtatgtcaa gtatgtcaca    9000
tgaagaaaat gtgaaattca agagtaatcc acacgtgaga aactagacaa tgtacattca    9060
tgtgttctct tgaaaggaaa gggagagctg taagcttcac tctgtcctac accggagaaa    9120
agcaggaata actttaccgt ggaaataatg tttagctttt atcagagaaa attgtccttc    9180
tagagcatag agtcccaaaa ctcaattctg gttttcccct gttttttttt ttttttttt    9240
tcccaacata tgaactgcag catatcactt tttctttttg tgcctcaggt tcctcacctg    9300
taaaattgaa aaatatatgt attaataata ttattaataa taataatggt aatgtagtac    9360
ttgtttgtaa agcactttga gatccttggt tgaaaggcac cataggagtg ccaagtatta    9420
ttatgtggcc aagggggtta tttaaactgt cagttcccaa aggccaggaa aggttggggt    9480
cattttctt aaagacgagc tgtaaatatc aactaggcag ccaatagtgt tgactatgaa    9540
gatgcaaaac tattactagg ctgataaaat catagtttct taatggctac caataaggca    9600
aatatcacaa taataaacgc caaattcctt agggcggact atttgacaac cacatggaaa    9660
actttggggg aggcatgagg ggggaacatc tcaaaatgcc aatgtaaaat ttaacttaca    9720
gcaatattca ccagcagaaa atgtctttca tatggaatga tttcatgttg ctaagaaaaa    9780
gaattcaatt tgtagtcctg atttgaatac tagaatgttg gctataatag ttctgttctt    9840
acaacacatg aaatttttTc gttttatttt atttTgtttt catagtgcat gttcatttct    9900
```

-continued

```
actcacaaac atgttcttgg tgtatttctt atgcaaacaa tcttcaggca gcaaagatgt    9960
ctgttacatc taaacttgaa taataaagtt ttccaccagt tacaca                  10006
```

<210> SEQ ID NO 21
<211> LENGTH: 1281
<212> TYPE: PRT
<213> ORGANISM: Homo sapiens

<400> SEQUENCE: 21

| Met | Val | Arg | Lys | Lys | Asn | Pro | Pro | Leu | Arg | Asn | Val | Ala | Ser | Glu | Gly |
|---|---|---|---|---|---|---|---|---|---|---|---|---|---|---|---|
| 1 | | | | 5 | | | | | 10 | | | | | 15 | |

| Glu | Gly | Gln | Ile | Leu | Glu | Pro | Ile | Gly | Thr | Glu | Ser | Lys | Val | Ser | Gly |
|---|---|---|---|---|---|---|---|---|---|---|---|---|---|---|---|
| | | | 20 | | | | | 25 | | | | | 30 | | |

| Lys | Asn | Lys | Glu | Phe | Ser | Ala | Asp | Gln | Met | Ser | Glu | Asn | Thr | Asp | Gln |
|---|---|---|---|---|---|---|---|---|---|---|---|---|---|---|---|
| | | 35 | | | | | 40 | | | | | 45 | | | |

| Ser | Asp | Ala | Ala | Glu | Leu | Asn | His | Lys | Glu | His | Ser | Leu | His | Val |
|---|---|---|---|---|---|---|---|---|---|---|---|---|---|---|
| | 50 | | | | | 55 | | | | | 60 | | | |

Gln Asp Pro Ser Ser Ser Lys Lys Asp Leu Lys Ser Ala Val Leu
65                  70                  75                  80

Ser Glu Lys Ala Gly Phe Asn Tyr Glu Ser Pro Ser Lys Gly Gly Asn
                85                  90                  95

Phe Pro Ser Phe Pro His Asp Glu Val Thr Asp Arg Asn Met Leu Ala
            100                 105                 110

Phe Ser Phe Pro Ala Ala Gly Gly Val Cys Glu Pro Leu Lys Ser Pro
        115                 120                 125

Gln Arg Ala Glu Ala Asp Asp Pro Gln Asp Met Ala Cys Thr Pro Ser
    130                 135                 140

Gly Asp Ser Leu Glu Thr Lys Glu Asp Gln Lys Met Ser Pro Lys Ala
145                 150                 155                 160

Thr Glu Glu Thr Gly Gln Ala Gln Ser Gly Gln Ala Asn Cys Gln Gly
                165                 170                 175

Leu Ser Pro Val Ser Val Ala Ser Lys Asn Pro Gln Val Pro Ser Asp
            180                 185                 190

Gly Gly Val Arg Leu Asn Lys Ser Lys Thr Asp Leu Leu Val Asn Asp
        195                 200                 205

Asn Pro Asp Pro Ala Pro Leu Ser Pro Glu Leu Gln Asp Phe Lys Cys
    210                 215                 220

Asn Ile Cys Gly Tyr Gly Tyr Tyr Gly Asn Asp Pro Thr Asp Leu Ile
225                 230                 235                 240

Lys His Phe Arg Lys Tyr His Leu Gly Leu His Asn Arg Thr Arg Gln
                245                 250                 255

Asp Ala Glu Leu Asp Ser Lys Ile Leu Ala Leu His Asn Met Val Gln
            260                 265                 270

Phe Ser His Ser Lys Asp Phe Gln Lys Val Asn Arg Ser Val Phe Ser
        275                 280                 285

Gly Val Leu Gln Asp Ile Asn Ser Ser Arg Pro Val Leu Leu Asn Gly
    290                 295                 300

Thr Tyr Asp Val Gln Val Thr Ser Gly Gly Thr Phe Ile Gly Ile Gly
305                 310                 315                 320

Arg Lys Thr Pro Asp Cys Gln Gly Asn Thr Lys Tyr Phe Arg Cys Lys
                325                 330                 335

Phe Cys Asn Phe Thr Tyr Met Gly Asn Ser Ser Thr Glu Leu Glu Gln
            340                 345                 350

```
His Phe Leu Gln Thr His Pro Asn Lys Ile Lys Ala Ser Leu Pro Ser
            355                 360                 365

Ser Glu Val Ala Lys Pro Ser Glu Lys Asn Ser Asn Lys Ser Ile Pro
        370                 375                 380

Ala Leu Gln Ser Ser Asp Ser Gly Asp Leu Gly Lys Trp Gln Asp Lys
385                 390                 395                 400

Ile Thr Val Lys Ala Gly Asp Asp Thr Pro Val Gly Tyr Ser Val Pro
                405                 410                 415

Ile Lys Pro Leu Asp Ser Ser Arg Gln Asn Gly Thr Glu Ala Thr Ser
            420                 425                 430

Tyr Tyr Trp Cys Lys Phe Cys Ser Phe Cys Glu Ser Ser Ser Ser
        435                 440                 445

Leu Lys Leu Leu Glu His Tyr Gly Lys Gln His Gly Ala Val Gln Ser
450                 455                 460

Gly Gly Leu Asn Pro Glu Leu Asn Asp Lys Leu Ser Arg Gly Ser Val
465                 470                 475                 480

Ile Asn Gln Asn Asp Leu Ala Lys Ser Ser Glu Gly Glu Thr Met Thr
                485                 490                 495

Lys Thr Asp Lys Ser Ser Gly Ala Lys Lys Asp Phe Ser Ser
            500                 505                 510

Lys Gly Ala Glu Asp Asn Met Val Thr Ser Tyr Asn Cys Gln Phe Cys
        515                 520                 525

Asp Phe Arg Tyr Ser Lys Ser His Gly Pro Asp Val Ile Val Val Gly
        530                 535                 540

Pro Leu Leu Arg His Tyr Gln Gln Leu His Asn Ile His Lys Cys Thr
545                 550                 555                 560

Ile Lys His Cys Pro Phe Cys Pro Arg Gly Leu Cys Ser Pro Glu Lys
                565                 570                 575

His Leu Gly Glu Ile Thr Tyr Pro Phe Ala Cys Arg Lys Ser Asn Cys
            580                 585                 590

Ser His Cys Ala Leu Leu Leu His Leu Ser Pro Gly Ala Ala Gly
        595                 600                 605

Ser Ser Arg Val Lys His Gln Cys His Gln Cys Ser Phe Thr Thr Pro
        610                 615                 620

Asp Val Asp Val Leu Leu Phe His Tyr Glu Ser Val His Glu Ser Gln
625                 630                 635                 640

Ala Ser Asp Val Lys Gln Glu Ala Asn His Leu Gln Gly Ser Asp Gly
                645                 650                 655

Gln Gln Ser Val Lys Glu Ser Lys Glu His Ser Cys Thr Lys Cys Asp
            660                 665                 670

Phe Ile Thr Gln Val Glu Glu Ile Ser Arg His Tyr Arg Arg Ala
        675                 680                 685

His Ser Cys Tyr Lys Cys Arg Gln Cys Ser Phe Thr Ala Ala Asp Thr
        690                 695                 700

Gln Ser Leu Leu Glu His Phe Asn Thr Val His Cys Gln Glu Gln Asp
705                 710                 715                 720

Ile Thr Thr Ala Asn Gly Glu Glu Asp Gly His Ala Ile Ser Thr Ile
                725                 730                 735

Lys Glu Glu Pro Lys Ile Asp Phe Arg Val Tyr Asn Leu Leu Thr Pro
            740                 745                 750

Asp Ser Lys Met Gly Glu Pro Val Ser Glu Ser Val Val Lys Arg Glu
        755                 760                 765

Lys Leu Glu Glu Lys Asp Gly Leu Lys Glu Lys Val Trp Thr Glu Ser
```

-continued

```
            770                 775                 780
Ser Ser Asp Asp Leu Arg Asn Val Thr Trp Arg Gly Ala Asp Ile Leu
785                 790                 795                 800

Arg Gly Ser Pro Ser Tyr Thr Gln Ala Ser Leu Gly Leu Leu Thr Pro
                    805                 810                 815

Val Ser Gly Thr Gln Glu Gln Thr Lys Thr Leu Arg Asp Ser Pro Asn
                    820                 825                 830

Val Glu Ala Ala His Leu Ala Arg Pro Ile Tyr Gly Leu Ala Val Glu
                    835                 840                 845

Thr Lys Gly Phe Leu Gln Gly Ala Pro Ala Gly Gly Glu Lys Ser Gly
850                 855                 860

Ala Leu Pro Gln Gln Tyr Pro Ala Ser Gly Glu Asn Lys Ser Lys Asp
865                 870                 875                 880

Glu Ser Gln Ser Leu Leu Arg Arg Arg Gly Ser Gly Val Phe Cys
                    885                 890                 895

Ala Asn Cys Leu Thr Thr Lys Thr Ser Leu Trp Arg Lys Asn Ala Asn
                    900                 905                 910

Gly Gly Tyr Val Cys Asn Ala Cys Gly Leu Tyr Gln Lys Leu His Ser
                    915                 920                 925

Thr Pro Arg Pro Leu Asn Ile Ile Lys Gln Asn Asn Gly Glu Gln Ile
            930                 935                 940

Ile Arg Arg Arg Thr Arg Lys Arg Leu Asn Pro Glu Ala Leu Gln Ala
945                 950                 955                 960

Glu Gln Leu Asn Lys Gln Gln Arg Gly Ser Asn Glu Glu Gln Val Asn
                    965                 970                 975

Gly Ser Pro Leu Glu Arg Arg Ser Glu Asp His Leu Thr Glu Ser His
                    980                 985                 990

Gln Arg Glu Ile Pro Leu Pro Ser Leu Ser Lys Tyr Glu Ala Gln Gly
            995                 1000                1005

Ser Leu Thr Lys Ser His Ser Ala Gln Gln Pro Val Leu Val Ser Gln
    1010                1015                1020

Thr Leu Asp Ile His Lys Arg Met Gln Pro Leu His Ile Gln Ile Lys
1025                1030                1035                1040

Ser Pro Gln Glu Ser Thr Gly Asp Pro Gly Asn Ser Ser Val Ser
                    1045                1050                1055

Glu Gly Lys Gly Ser Ser Glu Arg Gly Ser Pro Ile Glu Lys Tyr Met
            1060                1065                1070

Arg Pro Ala Lys His Pro Asn Tyr Ser Pro Pro Gly Ser Pro Ile Glu
            1075                1080                1085

Lys Tyr Gln Tyr Pro Leu Phe Gly Leu Pro Phe Val His Asn Asp Phe
    1090                1095                1100

Gln Ser Glu Ala Asp Trp Leu Arg Phe Trp Ser Lys Tyr Lys Leu Ser
1105                1110                1115                1120

Val Pro Gly Asn Pro His Tyr Leu Ser His Val Pro Gly Leu Pro Asn
            1125                1130                1135

Pro Cys Gln Asn Tyr Val Pro Tyr Pro Thr Phe Asn Leu Pro Pro His
            1140                1145                1150

Phe Ser Ala Val Gly Ser Asp Asn Asp Ile Pro Leu Asp Leu Ala Ile
            1155                1160                1165

Lys His Ser Arg Pro Gly Pro Thr Ala Asn Gly Ala Ser Lys Glu Lys
    1170                1175                1180

Thr Lys Ala Pro Pro Asn Val Lys Asn Glu Gly Pro Leu Asn Val Val
1185                1190                1195                1200
```

```
                                    -continued

Lys Thr Glu Lys Val Asp Arg Ser Thr Gln Asp Glu Leu Ser Thr Lys
            1205                1210                1215

Cys Val His Cys Gly Ile Val Phe Leu Asp Glu Val Met Tyr Ala Leu
        1220                1225                1230

His Met Ser Cys His Gly Asp Ser Gly Pro Phe Gln Cys Ser Ile Cys
    1235                1240                1245

Gln His Leu Cys Thr Asp Lys Tyr Asp Phe Thr Thr His Ile Gln Arg
    1250                1255                1260

Gly Leu His Arg Asn Asn Ala Gln Val Glu Lys Asn Gly Lys Pro Lys
1265                1270                1275                1280

Glu
```